(12) United States Patent
Gellermann et al.

(10) Patent No.: US 8,326,405 B2
(45) Date of Patent: *Dec. 4, 2012

(54) IMAGING OF MACULAR PIGMENT DISTRIBUTIONS

(75) Inventors: Werner Gellermann, Salt Lake City, UT (US); Mohsen Sharifzadeh, Salt Lake City, UT (US)

(73) Assignee: The University of Utah Research Foundation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/316,364

(22) Filed: Dec. 9, 2011

(65) Prior Publication Data
US 2012/0081668 A1 Apr. 5, 2012

Related U.S. Application Data

(63) Continuation of application No. 12/424,208, filed on Apr. 15, 2009, now Pat. No. 8,078,267, which is a continuation of application No. 11/416,915, filed on May 3, 2006, now abandoned, which is a continuation-in-part of application No. 11/018,403, filed on Dec. 21, 2004.

(51) Int. Cl.
*A61B 6/00* (2006.01)
(52) U.S. Cl. ........ 600/475; 600/407; 600/476; 600/477; 607/88; 356/317; 351/206; 351/221
(58) Field of Classification Search .................. 600/407, 600/475, 476, 477; 607/88; 356/317; 351/206, 351/221
See application file for complete search history.

(56) References Cited

U.S. PATENT DOCUMENTS

| | | | |
|---|---|---|---|
| 5,304,170 | A | 4/1994 | Green |
| 5,697,373 | A | 12/1997 | Richards-Kortum et al. |
| 5,873,831 | A | 2/1999 | Bernstein et al. |
| 6,205,354 | B1 | 3/2001 | Gellerman et al. |
| 6,276,798 | B1 | 8/2001 | Gil et al. |
| 6,315,412 | B1 | 11/2001 | Snodderly et al. |
| 6,800,086 | B2 | 10/2004 | Strong |
| 7,648,239 | B2 | 1/2010 | Spaide |

(Continued)

OTHER PUBLICATIONS

Delori, "Macular Pigment Density Measured by Autofluorescence Spectrometry: Comparison with Reflectometry and Heterochromatic Flicker Photometry," J. Opt. Soc. Am A, vol. 18, No. 6, Jun. 2001, 1212-1230.

(Continued)

*Primary Examiner* — Brian Casler
*Assistant Examiner* — Joel Lamprecht
(74) *Attorney, Agent, or Firm* — Austin Rapp & Hardman

(57) ABSTRACT

Macular pigments are measured by spectrally selective lipofuscin detection. Light from a light source that emits light at a selected range of wavelengths that overlap the absorption band of macular carotenoids is directed onto macular tissue of an eye for which macular pigment levels are to be measured. Emitted light is then collected from the macular tissue. The collected light is filtered so that the collected light includes lipofuscin emission from the macular tissue at an excitation wavelength that lies outside the macular pigment absorption range and outside the excitation range of interfering fluorophores. The collected light is quantified at each of a plurality of locations in the macular tissue and the macular pigment levels in the macular tissue are determined from the differing lipofuscin emission intensities in the macula and peripheral retina.

18 Claims, 18 Drawing Sheets

Lutein

Zeaxanthin

U.S. PATENT DOCUMENTS

| | | | |
|---|---|---|---|
| 8,078,267 B2 * | 12/2011 | Gellerman et al. | 600/476 |
| 2001/0009926 A1 | 7/2001 | Howard et al. | |
| 2002/0173832 A1 | 11/2002 | Strong | |
| 2002/0183302 A1 | 12/2002 | Strong et al. | |
| 2002/0193948 A1 | 12/2002 | Schweitzer et al. | |
| 2003/0004418 A1 | 1/2003 | Marmorstein | |
| 2003/0130579 A1 | 7/2003 | McClane et al. | |
| 2005/0010115 A1 | 1/2005 | Bone et al. | |
| 2007/0088078 A1 | 4/2007 | Dushenkov et al. | |

OTHER PUBLICATIONS

Delori, "Age-Related Accumulation and Spatial Distribution of Lipofuscin in RPE on Normal Subjects," Investigative Ophthalmology & Visual Sciences, Jul. 2001, vol. 42, No. 8, 1855-1866.

Delori, "Autofluorescence Method to Measure Macular Pigment Optical Densities Fluorometry and Autofluorescence Imaging," Archives of Biochemistry and Biophysics 430 (2004) 156-162.

Delori, "Bimodal Spatial Distribution of Macular Pigment: Evidence of a Gender Relationship," J. Opt. Soc. Am A, No. 28, No. 3, Mar. 2006, 521-538.

Framme, "Noninvasive Imaging and Monitoring of Retinal Pigment Epithelium Patterns Using Fundus Autofluorescence—Review," Current Medical Imaging Reviews, 2005, I,,89-103.

Van Norren, "Measuring Macular Pigment Optical Density with Undilated Pupil in One Second," Poster Presentation, Ophthalmic Res. 36 Suppl. 1, 117, (2004).

Robson, "Macular Pigment Density and Distribution: Comparison of Fundus Autofluorescence with Minimum Motion Photometry," Vision Research 43 (2003), 1765-1775.

Robson, "Comparison of Fundus Autofluorescence and Minimum-Motion Measurements of Macular Pigment Distribution Profiles Derived from Identical Retinal Areas," Perception, 2005, vol. 34, 1029-1034.

Trieschmann, "Macular Pigment: Quantitative Analysis on Autofluorescence Images," Graefe's Arch Clin Exp Opthalmol (2003) 241:1006-1012.

Sharifzadeh, "Nonmydriatic Fluorescence-Based Quantitative Imaging of Human Macular Pigment Distributions," J Opt Am A, vol. 23 No. 10, Oct. 2006, 2373-2387.

Spaide, "Fundus Autofluorescence and Age Related Macular Degeneration," Ophthalmology, vol. 110, No. 2, Feb. 2003, 392-399.

Spaide, "Optimized Filters for Fundus Autofluorescence Imaging" Retina Today, Apr. 2009, 79-81.

Trieschmann, "Macular Pigment Optical Density Measurement in Autofluorescence Imaging: Comparison of One-and Two-Wavelength Methods," Graefes Arch Clin Exp Ophthalmol, vol. 244, No. 12, Dec. 2006, 1565-1574.

Wustemeyer, "Macular Pigment Density in Healthy Subjects Quantified with a Modified Confocal Scanning Laser Ophthalmoscope" Graefes Arch Clin Exp Ophthalmol, vol. 241, No. 8, Aug. 2003, 647-651.

Seth, "Assessing Macular Pigment from SLO Images" Doc Ophthalm, vol. 108, No. 3, May 2004, 197-202.

Dietzel, "The Ringlike Structure of Macular Pigment in Age-Related Maculopathy: Results from the Muenster Aging and Macular Study (MARS)," IOVS, vol. 52, No. 11, Oct. 2011, 8016-8024.

Nolan, "Spatial Profile of Macular Pigment and its Relationship to Foveal Architecture," IOVS, vol. 49, No. 5, May 2008, 2134-2142.

Berendschot, "Macular Pigment Shows Ringlike Structures," IOVS, vol. 47, No. 2, Feb. 2006, 709-714.

* cited by examiner

Lutein

Zeaxanthin

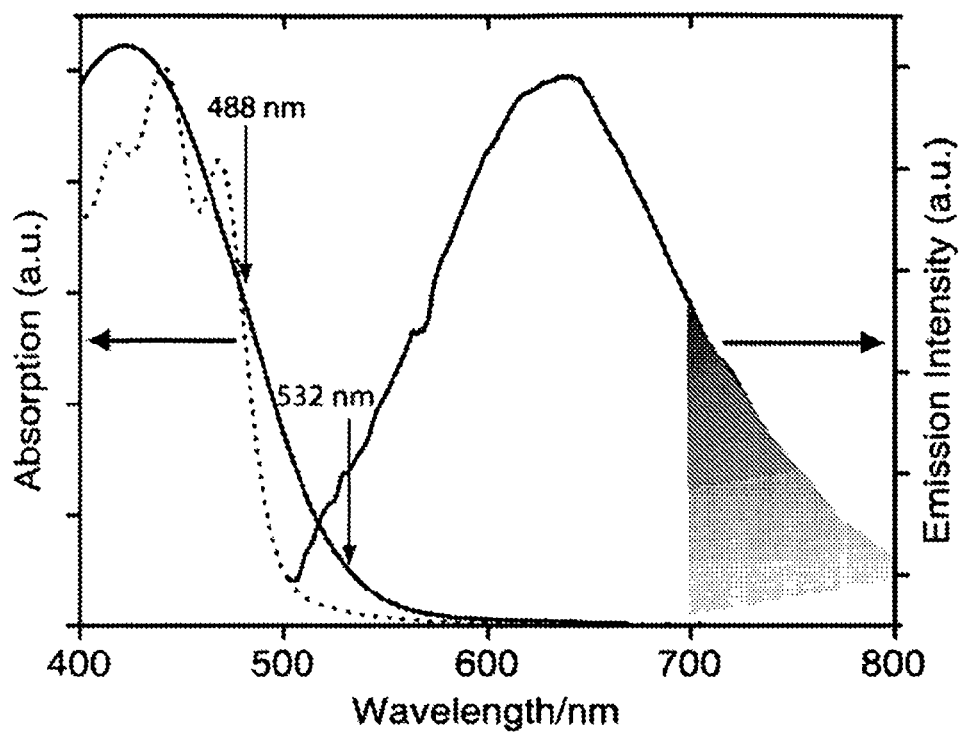
FIG. 2A
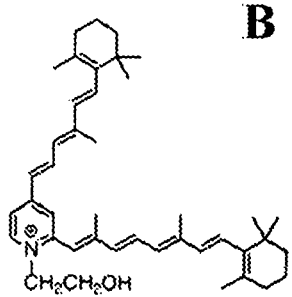 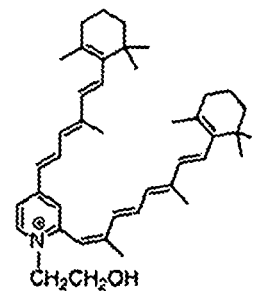 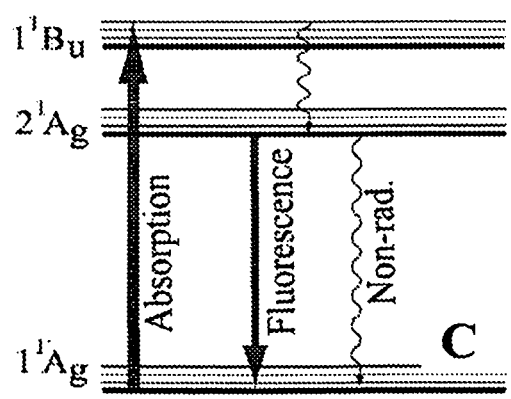
FIG. 2B                    FIG. 2C (a)

(b)

(c)

(d)

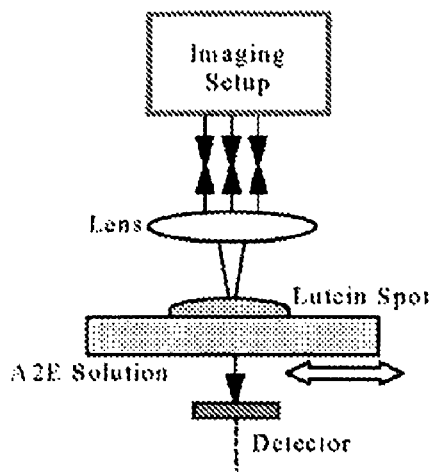
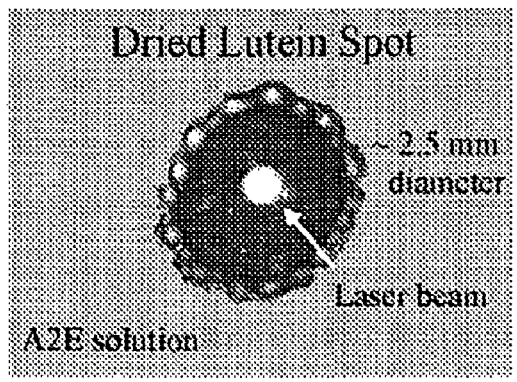
FIG. 9A  FIG. 9B
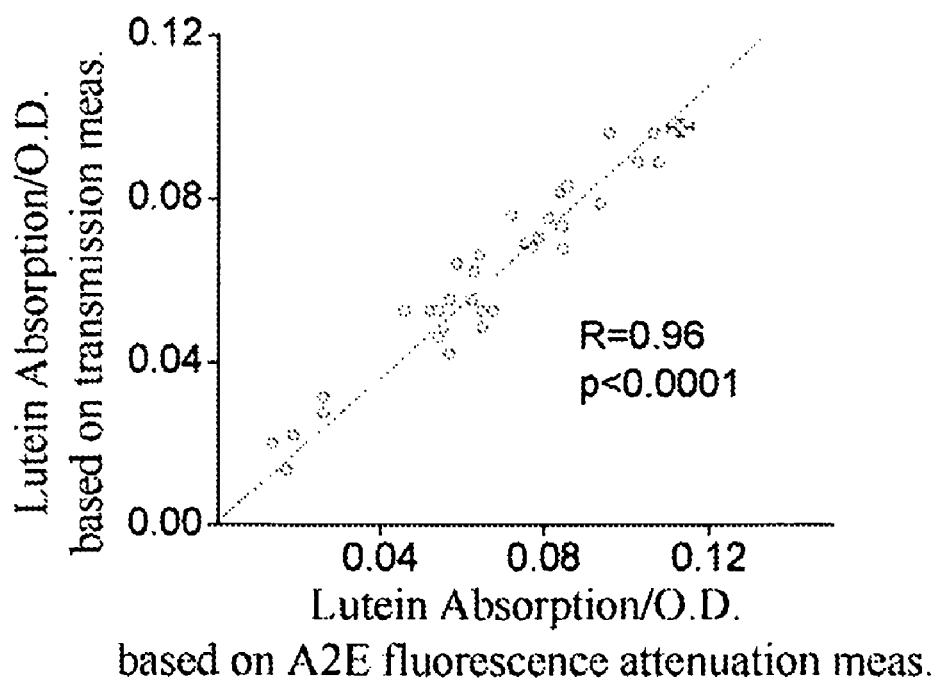
FIG. 9C

IMAGING OF MACULAR PIGMENT DISTRIBUTIONS

CROSS-REFERENCE TO RELATED APPLICATIONS

This application is a continuation of U.S. patent application Ser. No. 12/424,208, filed Apr. 15, 2009, entitled "IMAGING OF MACULAR PIGMENT DISTRIBUTIONS," now issued as U.S. Pat. No. 8,078,267, which is a continuation of U.S. patent application Ser. No. 11/416,915, filed May 3, 2006, entitled "IMAGING OF MACULAR PIGMENT DISTRIBUTIONS," now abandoned, which is a continuation-in-part of U.S. patent application Ser. No. 11/018,403, filed Dec. 21, 2004, entitled "Methods and Apparatus for Detection of Carotenoids for Macular Tissue", which are incorporated herein by reference.

BACKGROUND OF THE INVENTION

1. The Field of the Invention

The present invention relates to techniques for optically measuring levels of chemical compounds in biological tissues. More particularly, the invention relates to the noninvasive optical detection and measurement of levels of macular carotenoids and related chemical substances using spectrally selective fluorescence spectroscopy of lipofuscin.

2. The Relevant Technology

Macular pigment ("MP") is a collection of biological compounds concentrated in a small region in the center of the retina that provides high-acuity vision. Comprised of the carotenoid compounds lutein and zeaxanthin, MP is thought to play a protective role in the prevention or delay of age-related macular degeneration ("AMD"), the leading cause of irreversible blindness in the elderly in the Western world. Epidemiological studies analyzing carotenoid levels via dietary surveys and serum assays have shown that there is an inverse correlation between high dietary intakes and blood levels of lutein and zeaxanthin and risk of advanced AMD. Furthermore, several studies, including resonance Raman clinical studies and a high performance liquid chromatography ("HPLC") analysis of human cadaver eyes with and without a known history of AMD, have demonstrated a correlation between levels of lutein and zeaxanthin and AMD.

The standard methods that have been used for measuring carotenoids are through high-performance liquid chromatography (HPLC) techniques. Such techniques require that large amounts of tissue sample be removed from the patient for subsequent analysis and processing, which typically takes at least 24 hours to complete. In the course of these types of analyses, the tissue is damaged, if not completely destroyed. As a result, there is a strong interest to develop non-invasive detection techniques for MP in the living human retina. Such techniques could be used, for example, in large-scale monitoring studies of dietary and/or nutritional interventions designed to raise MP levels, and potentially help protect a large fraction of the population from developing this debilitating disease.

Currently, the most commonly used noninvasive method for measuring human MP levels is a subjective psychophysical heterochromatic flicker photometry test involving color intensity matching of a light beam aimed at the fovea and another aimed at the perifoveal area. However, this method is rather time consuming and requires an alert, cooperative subject with good visual acuity. This method can also exhibit a high intrasubject variability when macular pigment densities are low or if significant macular pathology is present. Thus, the usefulness of this method for assessing macular pigment levels in the elderly population most at risk for AMD is severely limited. Nevertheless, researchers have used flicker photometry to investigate important questions such as variation of macular pigment density with age and diet.

A number of objective techniques for the measurement of MP in the human retina have been explored recently as alternatives to the subjective psychophysical tests. The underlying optics principles of these techniques are either based on fundus reflection or fundus fluorescence (autofluorescence) spectroscopy.

One of the MP imaging approaches is based on fundus reflectance techniques. There are two variants in which this method is implemented. In one variant, the reflectance of a broad band light source from the sclera is compared for a foveal and perifoveal spot and the spectral contribution of the absorbance by MP is calculated. In a second variant, no reference at a peripheral site is needed. Only a foveal field is used, and MP levels are derived from a model fit that takes into account the absorption and scattering coefficients of all retinal layers traversed in a double-path succession by the light.

Some reflectance based imaging variants are based on scanning laser ophthalmoscopes (SLOs). Argon laser lines at 488 and 514 nm are used to generate monochromatic digital reflection images from the retina at MP "on peak" and "off peak" spectral absorption positions, which are then digitally subtracted to display the MP absorption distribution. While reflectance based MP imaging is evolving as a viable clinical technique for subjects, a drawback of the technology is seen in the need for eyes in mydriasis (dilation of the pupil).

In autofluorescence spectroscopy, lipofuscin in the retinal pigment epithelium is excited with light within and outside the wavelength range of macular pigment absorption, but within the absorption range of lipofuscin. This can be realized, for example, with 488 nm and 532 nm light sources, respectively. The blue (488 nm) wavelength is absorbed both by macular pigment and lipofuscin; the green (532 nm) wavelength is absorbed only by lipofuscin. By measuring the lipofuscin fluorescence intensity levels for the foveal and peripheral retina regions, $I_{min}$ and $I_{max}$, respectively, for both excitation wavelengths, an estimate of the single-pass absorption of MP can be obtained. A disadvantage of the autofluoresecence technique is its low specificity. In principle, any absorber absorbing in the same wavelength range as the MP can artifactually attenuate the lipofuscin excitation, and thus lead to an erroneous mapping of the MP distribution and its concentration levels. This could be a serious drawback, particularly in the presence of retinal pathology (e.g. drusen, bleeding vessels, etc). Similarly, fluorescence from other compounds than lipofuscin could confound the results.

MP usually peaks in the center of the macula, the foveola, and drops off rapidly with increasing eccentricity. Absolute concentrations of MP are very high compared to other tissue sites, corresponding typically to 10-30 ng per macular punch biopsy (about 5 mm diameter). FIG. 1 illustrates the absorption spectrum of an excised, flat-mounted, human retina in the blue/green wavelength region, showing typical absorption characteristics of carotenoid macular pigment (solid curve at left). The retinal pigment epithelium of the retina was removed for this measurement, and the spectrum was measured through a 1 mm aperture. In spite of the very thin retinal tissue layer, the optical density reaches an average value of about 0.3 above background, which explains the origin of the strong yellow coloration of the macula. Comparing the optical absorption of the macula with lutein and zeaxanthin solutions, one finds that the absorption behavior is remarkably similar, including the appearance of vibronic substructure, and that there is little overlap with potentially confounding other chromophores in the intact retina. The solid curve at right shows the fluorescence spectrum of a solution of lutein, obtained under excitation at 488 nm.

Optical excitation of MP leads to only very weak fluorescence since the excited lutein and zeaxanthin molecules relax very rapidly (within 200-250 fsec) to a lower lying excited state from which emission of light is parity forbidden (see FIG. 1C). The unusual ordering of the energy states is a unique feature of the polyene-like, .pi.-conjugated carotenoids having a large number of conjugated C.dbd.C double bonds (10 and 11 in lutein and zeaxanthin, respectively, see FIG. 1B). In fact, the quantum efficiency for a radiative transition from the $2\,^1Ag$ excited state to the $1\,^1Ag$ ground state is estimated to be as low as $10^{-5}$ to $10^{-4}$. Therefore, relaxation of the excited molecule back to the ground state occurs mostly via non-radiative transitions. The weak emission, observable only with very sensitive detection, has a small Stokes shift, and occurs in the green wavelength range centered at about 530 nm, as shown in FIG. 1 (solid curve at right).

Due to the weak fluorescence transitions, direct detection of MP using lutein or zeaxanthin fluorescence has not been realized to date. However, the virtual absence of intrinsic MP fluorescence makes it possible to detect instead the resonance Raman transitions of MP, even in living human eyes, which would otherwise be masked beyond detection by the fluorescence background. As a result, one method for the measurement of carotenoids and related chemical substances in biological tissue is by resonance Raman spectroscopy, for example as disclosed in U.S. Pat. No. 6,205,354, the disclosure of which is incorporated by reference herein in its entirety. Generally, Raman spectroscopy is a highly specific form of vibrational spectroscopy that identifies a Raman shift, which corresponds to an energy which is the fingerprint of the vibrational or rotational energy state of certain molecules. Typically, a molecule exhibits several characteristic Raman active vibrational or rotational energy states, and the measurement of the molecule's Raman spectrum thus provides a fingerprint of the molecule, i.e., it provides a molecule-specific series of spectrally sharp vibration or rotation peaks. The intensity of the Raman scattered light corresponds directly to the concentration of the molecule(s) of interest. In the case of Raman spectroscopy as applied to MP, this method detects the light that is Raman scattered from the MP carotenoid molecules at their 1525 cm.sup.−1 carbon-carbon double bond stretch frequency under resonant excitation in the MP absorption band. The Raman method measures the response of MP directly and has a very high molecule specificity.

Raman detection methods have the benefit of extremely high specificity for lutein and zeaxanthin, and therefore for MP. However, detecting only the absolute amount of MP, the Raman response is attenuated to some degree by the combined absorption and scattering of anterior ocular media, predominantly the lens.

Accordingly, improved methods and apparatus that quickly, safely, and accurately measure a human's macular carotenoid levels are needed.

BRIEF SUMMARY OF THE INVENTION

According to the invention, macular pigment ("MP") imaging based on lipofuscin fluorescence detection is useful as a relatively simple, objective and quantitative noninvasive optical technique suitable to rapidly screen MP levels and distributions in healthy humans with undilated pupils. The invention can be used in a direct and quantitative optical diagnostic technique, which uses low intensity illumination of intact tissue and provides high spatial resolution, allowing for precise quantification of the carotenoid levels in the tissue.

The detection of lipofuscin fluorescence, in combination with suitable signal processing, can be used to indirectly derive the concentrations and spatial distributions of MP in living human subjects. Particularly, the invention enables the elimination of the confounding effects of fluorophores, found mainly in the lens, in detected intensity maps. The confounding effect on the optically detected MP levels can be avoided by using a transmission filter in the fluorescence detection channel that limits the detection to wavelengths on the long-wavelength shoulder of the lipofuscin fluorescence spectrum. Using a direct, CCD based fluorescence imaging setup with suitable light excitation sources, like lasers, light emitting diodes (LEDs), or conventional light sources with suitable filters, and filtered signal detection, MP distributions can be measured within a fraction of a second through undilated eyes with high reproducibility.

The spatial and quantitative information of retinal MP levels simultaneously measurable with the lipofuscin-based technique without pupil dilation can be expected to be of tremendous value in screening of large populations. It can be a tool in studies investigating the influence of dietary supplements on MP levels and their distributions, and in research investigating the link between MP levels and retinal pathologies. Since the fluorescence based MP detection method is not influenced, in first order, by anterior media opacities, it could have a particular advantage over the Raman method in elderly subjects, which in general have higher lens opacities, and often reduced MP levels.

Accordingly, a first example embodiment of the invention is a method for measuring macular pigments. The method generally includes first providing a light source that emits light at a selected range of wavelengths that simultaneously overlaps the absorption band of macular carotenoids and the absorption band of lipofuscin. The light is directed from the light source onto macular tissue of an eye for which macular pigment levels are to be measured, light emitted from the macular tissue is collected, the collected light comprising lipofuscin emission from the macular tissue at an excitation wavelength that lies outside the macular pigment absorption range and outside the excitation range of interfering fluorophores. The collected light is quantified for each of a plurality of locations in the macular tissue and the lipofuscin emission intensities from each of a plurality of locations is thereby determined as well. Finally, the macular pigment levels in the macular tissue are determined from the differing lipofuscin emission intensities in the macula and peripheral retina. Further details and variants on this method are described elsewhere herein.

Another example method of the invention is also a method for measuring macular pigments. This method generally includes: providing a light source that emits light at a selected range of wavelengths that overlap the absorption band of macular carotenoids; directing light from the light source at an intensity of less than about 10 mJ/cm$^2$ for less than 500 msec onto macular tissue of an undilated eye for which macular pigment levels are to be measured; collecting light emitted from the macular tissue, the collected light comprising lipofuscin emission from the macular tissue at an excitation wavelength that lies outside the macular pigment absorption range and outside the excitation range of interfering fluorophores in the lens; quantifying the collected light from each of a plurality of locations in the macular tissue and thereby quantifying the lipofuscin emission intensities from each of a plurality of locations; determining the macular pigment levels in the macular tissue from the differing lipofuscin emission intensities in the macula and peripheral retina; and determining spatial extent and topographic concentration distribution of the macular pigments.

Yet another non limiting example embodiment of the invention is an apparatus for measuring macular pigments. The apparatus includes a light source that generates light at a wavelength that produces an autofluorescence lipofuscin emission. One or more light delivery optical components such as fibers, a shutter, lens filters, etc. are used for directing light from the light source to a subject's eye. Light collection optical components are used for receiving an autofluorescence lipofuscin emission from the subject's eye and routing the autofluorescence lipofuscin emission from the eye. An optical filter is configured for receiving the autofluorescence lipofuscin emission and is selective for passing light at a selected wavelength range such that fluorescence contributions from ocular media besides the macula are substantially blocked. An optical detector is configured for receiving the passed light from the optical filter and generating a signal indicative of the fluorescence intensities of the lipofuscin emission at a plurality of points on the subject's eye. A computing device can be used to determine intensities of the lipofuscin emission from the passed light at a plurality of points.

These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 2a illustrates the absorption and emission spectra of a methanolic solution of A2E, the main fluorophore of lipofuscin, shown as solid curves at left and right side of panel, respectively. The absorption spectrum of macular pigment is indicated as a dashed curve;

FIG. 2b illustrates molecular structures of A2E (left) and iso-A2E;

FIG. 2c is an energy level diagram for lipofuscin with optical transitions shown as arrows;

FIG. 9a is a top view schematic illustration of a setup used in the measurement of lutein concentrations in a tissue phantom consisting of a dried lutein spot located on the side wall of a thin cuvette filled with an optically thin A2E solution (O.D. about 0.35);

FIG. 9b is a side view schematic illustration of a setup used in the measurement of lutein concentrations in a tissue phantom consisting of a dried lutein spot located on the side wall of a thin cuvette filled with an optically thin A2E solution (O.D. about 0.35);

FIG. 9c is a plot illustrating optical densities of lutein concentrations measured for several dozen positions within the dried lutein spot, using simultaneous lipofuscin fluorescence attenuation and transmission measurements of the individual spots, showing excellent correlation (correlation coefficient $R=0.96$);

DETAILED DESCRIPTION OF THE PREFERRED EMBODIMENTS

Figure 1A:
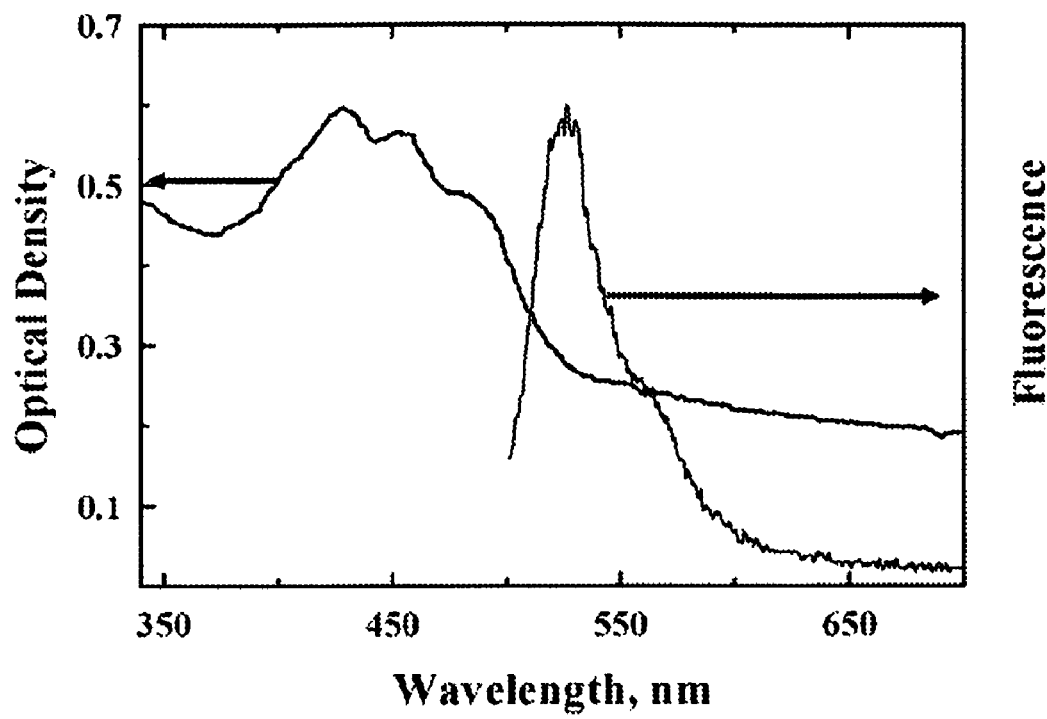
FIG. 1a illustrates the absorption spectrum of an excised, flat-mounted, human retina in the blue/green wavelength region, showing typical absorption characteristics of carotenoid macular pigment (solid curve at left) and the very weak fluorescence of macular pigment (solid curve at right) obtained when exciting them in their absorption band.
Figure 1B:
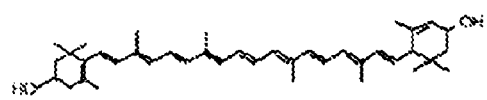
FIG. 1b illustrates the molecular structure of lutein and zeaxanthin.
Figure 1B:
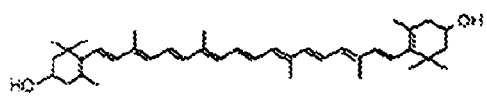
Figure 1C:
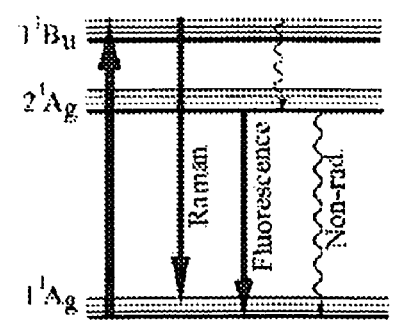
FIG. 1c is an energy level diagram of long-chain conjugated carotenoids like lutein or zeaxanthin, with optical and non-radiative transitions like excitation, Raman, and fluorescence, indicated as arrows.

According to the invention, lipofuscin fluorescence spectroscopy ("autofluorescence or AF spectroscopy") can be used to noninvasively and indirectly derive the concentrations and spatial distributions of MP in living mammals, e.g. human subjects. Conventional approaches suffer from the effects of fluorophores in the living human lens that have previously confounded lipofuscin fluorescence techniques. The fluorophores in the living human lens are simultaneously excited with the lipofuscin molecules to generate a strong fluorescence in the green/yellow wavelength range. According to one aspect of the invention, the confounding effect on the optically detected MP levels can be avoided by using a transmission filter in the fluorescence detection channel that limits the detection to wavelengths on the long-wavelength shoulder of the lipofuscin fluorescence spectrum. For example, using a direct, CCD based fluorescence imaging setup with laser excitation and filtered signal detection, the invention makes it possible to measure MP distributions within a fraction of a second with high reproducibility, while avoiding confounding effects of lens fluorescence.

Embodiments of the invention can be performed or used quickly in non-mydriatic conditions. A mydriatic is an agent which induces dilation of the pupil. Normally, mydriatic drugs such as tropicamide are used in ophthalmology to permit examination of the retina and other deep structures of the eye. Applying a mydriatic to examine the retina is inherently risky because it removes a protective defense of the body. The non-mydriatic uses of the invention can therefore provide a significant advantage by increasing the safety, speed, and frequency with which the tests can be performed.

Reference will now be made to the drawings to describe various aspects of exemplary embodiments of the invention. It is to be understood that the drawings are diagrammatic and schematic representations of such exemplary embodiments, and are not limiting of the present invention, nor are they necessarily drawn to scale.

In the following description, numerous specific details are set forth in order to provide a thorough understanding of the present invention. It will be obvious, however, to one skilled in the art that the present invention may be practiced without these specific details. In other instances, well-known aspects of the molecules and compositions discussed herein, the physics of light, and optical systems in general have not been described in particular detail in order to avoid unnecessarily obscuring the present invention.

Human retinal pigment epithelium contains the age pigment lipofuscin which accumulates in the lysosomal body of the RPE cells. Two components of lipofuscin exist that absorb strongly in the blue wavelength region and emit strongly in the orange-red region. They are two isomers of a bis-substituted pyridinium ring, and are termed A2E and iso-A2E, respectively. The structure of the molecules, their optical transitions, and their associated energy level scheme are shown in FIGS. 2a, 2b, and 2c.

The absorption spectrum of A2E partially overlaps with the absorption spectrum of the macular carotenoids, and its emission spectrum is broad, extending to wavelengths well beyond the absorption of carotenoids, as shown in FIG. 2a. Particularly, FIG. 2a is a graph of the absorption (solid curve at left) and emission spectra (solid curve at right) of A2E, the main fluorophore of lipofuscin, dissolved in methanol. The absorption peaks in the blue spectral range at about 430 nm, and the emission in the red spectral range at about 640 nm. The absorption of the macular pigments lutein and zeaxanthin is also indicated, as a dotted line, and shows that it essentially occurs in the same spectral range as that of lipofuscin, with the important exception that lipofuscin absorbs also to longer wavelengths compared to the macular pigments, so that a wavelength range exists on the long-wavelength shoulder of the lipofuscin absorption band where lipofuscin can excited exclusively without being attenuated by the macular pigment absorption. Two spectral positions of laser excitation lines, 488 nm and 532 nm, respectively, are shown as arrows. The 488 nm line is seen to overlap both the lipofuscin and the MP absorption on the long wavelength shoulder. The 532 nm line is outside the spectral absorption range of MP but overlaps that of lipofuscin.

It is possible, therefore, to excite the A2E emission within and outside the absorption range of MP. Similar to lutein and zeaxanthin, A2E has a conjugated carbon backbone. However, the conjugation length is shorter, interrupted by the central pyridinium ring, which shortens the conjugated carbon bond chain to two smaller chains with five double bonds each. This leads to an emission with a quantum efficiency of $10^{-2}$, which is about three orders of magnitude stronger than that reported for lutein and zeaxanthin. The in-vivo excitation spectrum of fundus autofluorescence is much broader than that of A2E, suggesting that other lipofuscin fluorophores contribute to fundus autofluorescence. Regarding its spatial distribution, it is known that the lipofuscin fluorescence at 15° from the fovea is 1.4-1.7 times higher than at the fovea and that there is a gradual increase in lipofuscin fluorescence with increasing eccentricity.

As will be described in greater detail elsewhere herein, the shading to the right of about 700 nm indicates the wavelength range where a long-wavelength pass filter used for the measurement of lipofuscin emission has reached transparency, limiting the detection of the lipofuscin emission intentionally only to wavelengths beyond about 700 nm.

Figure 3A:
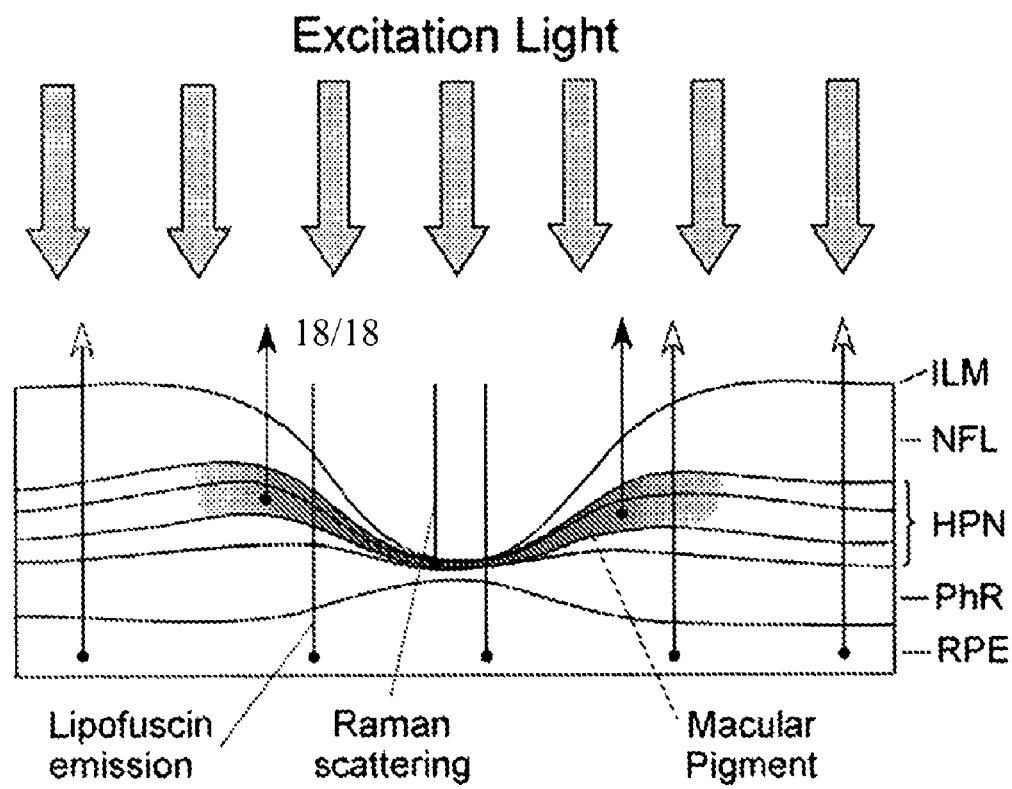
FIG. 3a is a schematic representation of retinal layers participating in light absorption, transmission, and scattering of excitation and emission light in the macular region.

With reference to FIG. 3a, excitation light, indicated by shaded arrows, is shown reaching a retina, where the MP levels are generally depicted as shaded areas. In MP Raman detection, which uses backscattering of excitation light from the MP-containing Henle fiber layer, detection is not influenced by deeper retinal layers as indicated by the limited depth of the filled arrows. In contrast, emission of lipofuscin used in autofluorescence-based measurements of MP has to traverse the photoreceptor (PhR) layer, and also deeper layers of the retina. Therefore, it has to take into account additional absorption and emission effects of these layers and their fluorophores.

As seen in resonance Raman detection experiments of MP, that detect the spectrally sharp C.dbd.C double bond 1525 $cm^{-1}$ stretching vibration Raman response of lutein and zeaxanthin (M), which occur at 527 nm under 488 nm excitation, a strong fluorescence background is superimposed on the Raman response in the 530 nm region. This fluorescence background varies strongly from subject to subject and exceeds in strength the background level expected from intrinsic lutein or zeaxanthin (MP) fluorescence. This background is a combination of lipofuscin fluorescence and fluorescence from anterior ocular media. In Raman detection, the broad fluorescence background can be easily fitted with a higher order polynomial and subtracted from the measured spectra.

In lipofuscin-based MP measurements, however, the extra fluorescence responses can be expected to play an interfering role. Methods of handling these extra fluorescence responses are therefore described below.

Figure 3B:
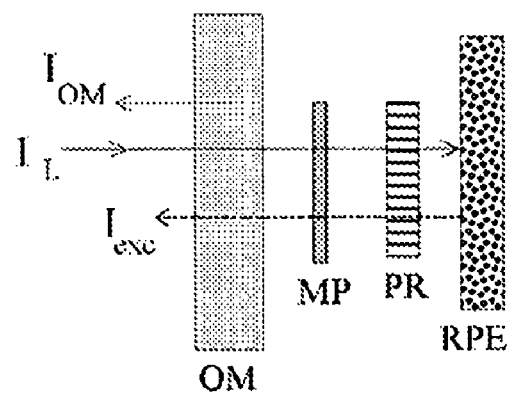
FIG. 3b is the schematics of anterior optical media and retinal layers traversed by excitation laser light, fluorescence from anterior optical media and fluorescence from lipofuscin.

The optical layers of interest traversed by the excitation light and the lipofuscin fluorescence are sketched in FIG. 3b. The fluorescence intensity in 180 degree detection geometry, $I_{Det}$, measured at a selected wavelength, $\lambda$, in the visible/near IR wavelength range, is in general given by $$I_{Det}(\lambda) = I_L(\lambda) \cdot T_{PR}(\lambda) \cdot T_{MP}(\lambda) \cdot T_{OM}(\lambda) + I_{OM}(\lambda), \quad (Eq.\ 1)$$

where $T(\lambda)$ is the transmission of the respective layer corresponding to photoreceptors, PR, macular pigment, MP, and anterior ocular media, OM, at the fluorescence wavelength, $\lambda$, $I_L$ is the lipofuscin fluorescence originating in the fovea, and $I_{OM}(\lambda)$ is the potentially overlapping fluorescence intensity of the OM layer at $\lambda$.

It is safe to assume that the photoreceptors do not generate any fluorescence, but their absorption cannot be neglected, in general. Under excitation with $I_{exc}$ at wavelength $\lambda_{exc}$, the lipofuscin fluorescence intensity $I_L(\lambda)$ is correlated with $I_{exc}$ according to $$I_L(\lambda_{exc},\lambda) = \eta_L(\lambda_{exc},\lambda) \cdot I_{exc}(\lambda_{exc}) \cdot T_{OM}(\lambda_{exc}) \cdot T_{MP}(\lambda_{exc}) \cdot T_{PR}(\lambda), \quad (Eq.\ 2)$$

and $I_{OM}$ is correlated with $I_{exc}$, according to $$I_{OM}(\lambda_{exc},\lambda) = \eta_{OM}(\lambda_{exc},\lambda) \cdot I_{exc}(\lambda_{exc}) \cdot (1 - T_{OM}), \quad (Eq.\ 3)$$

where $\eta_L(\lambda,\lambda_{exc})$ and $\eta_{OM}(\lambda,\lambda_{exc})$ are the fluorescence quantum efficiencies, respectively, of lipofuscin and the anterior ocular media.

Inserting equations (2) and (3) into (1), one obtains $$I_{Det}(\lambda_{exc},\lambda) = \eta_{MP}(\lambda_{exc},\lambda) \cdot I_{exc}(\lambda_{exc}) \cdot T_{OM}(\lambda_{exc}) \cdot T_{MP}(\lambda_{exc}) \cdot T_{PR}(\lambda_{exc}) \cdot T_{OM}(\lambda) \cdot T_{MP}(\lambda) \cdot T_{PR}(\lambda) + \eta_{OM}(\lambda_{exc},\lambda) \cdot I_{exc}(\lambda_{exc}) \cdot [1 - T_{OM}(\lambda)]. \quad (Eq.\ 4)$$

In general, it is impossible to extract the isolated MP transmission (absorption) from this complex relation between detector intensity and transmission/fluorescence terms of all layers. However, adopting a string of assumptions and approximations, it becomes possible to eliminate, in first order, several unwanted terms in (4), and to derive an approximation for the MP transmission (absorption) difference between fovea and perifovea.

First, as substantiated below (section 3), it is possible to largely block the detection of OM fluorescence by limiting the detection of lipofuscin fluorescence to near IR wavelengths. Only under this condition can the second term in (Eq. 4) can be ignored. Second, it is useful to reference the detected luminescence in the fovea to a measurement in the perifovea, and to determine this ratio for two excitation wavelengths $\lambda_1$ and $\lambda_2$ near the peak and just outside the MP absorption band, respectively. For the ratios of the MP transmissions in perifovea and fovea at the two wavelengths one then obtains $$\frac{I_{Det}^P(\lambda_{est},\lambda)}{I_{Det}^F(\lambda_{exc},\lambda)} = \frac{\eta_{MP}^P(\lambda_{exc},\lambda)}{\eta_{MP}^F(\lambda_{exc},\lambda)} \cdot \frac{T_{OM}^P(\lambda_{exc})T_{OM}^P(\lambda)}{T_{OM}^F(\lambda_{exc})T_{OM}^F(\lambda)} \cdot \frac{T_{MP}^P(\lambda_{exc})T_{MP}^P(\lambda)}{T_{MP}^F(\lambda_{exc})T_{MP}^F(\lambda)} \cdot \frac{T_{PR}^P(\lambda_{exc})T_{PR}^P(\lambda)}{T_{PR}^F(\lambda_{exc})T_{PR}^F(\lambda)} \quad (Eq.\ 5)$$

If one assumes that the lipofuscin composition is constant across the posterior pole, the quantum efficiency ratio term $$\left(\frac{\eta_{MP}^P(\lambda_1,\lambda)}{\eta_{MP}^F(\lambda_1,\lambda)} \bigg/ \frac{\eta_{MP}^P(\lambda_2,\lambda)}{\eta_{MP}^F(\lambda_2,\lambda)}\right)$$

is eliminated. If one further assumes that there is no difference between foveal and perifoveal lens transmission terms cancel out. Furthermore, if one insures that the excitation light beam profiles are identical for the two wavelengths, they cancel out, too. One then obtains the much simplified expression $$\left(\frac{I_{Det}^P(\lambda_1,\lambda)}{I_{Det}^F(\lambda_1,\lambda)}\right) \bigg/ \left(\frac{I_{Det}^P(\lambda_2,\lambda)}{I_{Det}^F(\lambda_2,\lambda)}\right) = \left(\frac{T_{MP}^P(\lambda_1)}{T_{MP}^F(\lambda_1)} \bigg/ \frac{T_{MP}^P(\lambda_2)}{T_{MP}^F(\lambda_2)}\right) \cdot \left(\frac{T_{PR}^P(\lambda_1)}{T_{PR}^F(\lambda_1)} \bigg/ \frac{T_{PR}^P(\lambda_2)}{T_{PR}^F(\lambda_2)}\right). \quad (Eq.\ 6)$$

Referencing the transmissions of the excitation light at the $\lambda_1$ and $\lambda_2$ positions to the transmission values in the peak of the MP absorption band, 460 nm, with respective extinction coefficients $K_{MP}(\lambda_1)$ and $K_{MP}(\lambda_2)$, where $$T_{MP}^{P,F}(\lambda_1) = T_{MP}^{P,F}(460)^{K(\lambda_1)}, T_{MP}^{P,F}(\lambda_2) = T_{MP}^{P,F}(460)^{K(\lambda_2)},$$

the right side of (Eq. 6) reduces to $$O.D._{MP}^F(\lambda_{460}) - O.D._{MP}^P(\lambda_{460}) = \quad (Eq.\ 7)$$
$$\frac{1}{\Delta K}\left\{\log\left(\frac{I_{Det}^P(\lambda_1,\lambda)}{I_{Det}^F(\lambda_1,\lambda)}\right) - \log\left(\frac{I_{Det}^P(\lambda_2,\lambda)}{I_{Det}^F(\lambda_2,\lambda)}\right)\right\} - \frac{1}{\Delta K}\log\left(\frac{T_{PR}^P(\lambda_1)}{T_{PR}^F(\lambda_1)} \bigg/ \frac{T_{PR}^P(\lambda_2)}{T_{PR}^F(\lambda_2)}\right).$$

If one assumes in addition that the photoreceptors can be completely bleached in the measurements ($T_{PR}$=100%), the second term can be neglected. Then the MP optical density difference between fovea and perifovea is given by $$O.D._{MP}^F(\lambda_{460}) - O.D._{MP}^P(\lambda_{460}) = \quad (Eq.\ 8)$$
$$\frac{1}{\Delta K}\left\{\log\left(\frac{I_{Det}^P(\lambda_1,\lambda)}{I_{Det}^F(\lambda_1,\lambda)}\right) - \log\left(\frac{I_{Det}^P(\lambda_2,\lambda)}{I_{Det}^F(\lambda_2,\lambda)}\right)\right\},$$

i.e. it can be approximated by the log differences of foveal and perifoveal fluorescence intensities.

It should be mentioned that besides lipofuscin detection at near infrared wavelength other approaches are possible to minimize the effects of media fluorescence. These include confocal optics, separation of excitation and detection beams through the lens, and correction for lens fluorescence.

It is instructive to compare the derived expressions with the expression for the MP signal intensity obtained with the Raman method. Since the Raman response originates directly in the MP layer, deeper layers do not play a role in the excitation and emission paths. Only the anterior optical media are traversed, resulting in $$I_S = T_{OM}(\lambda_{exc}) \cdot T_{OM}(\lambda_{Raman}) \cdot N(E_I) \cdot \sigma_R \cdot I_{exc}(\lambda_{exc}) + \eta_{OM}(\lambda_{exc},\lambda_{Raman}) \cdot I_{exc}(\lambda_{exc}) \cdot [1 - T_{OM}(\lambda_{Raman})]. \quad (Eq.\ 9)$$

Here, $I_S$ is the Raman scattered light intensity, $N(E_I)$ is the concentration of MP molecules, $\sigma_R$ is the Raman scattering cross section, and $I_{exc}$ is the laser excitation intensity. No assumptions regarding photoreceptor bleaching have to be made, and since the fluorescence of the lens is easily distinguishable from the spectrally sharp Raman response of MP, it can be easily subtracted. On the other hand, since very little MP exists outside the macula area, foveal Raman measurements can not be referenced to perifoveal levels, and lens absorptions as well as all anterior media scattering will reduce the observed Raman intensities.

Figure 4:
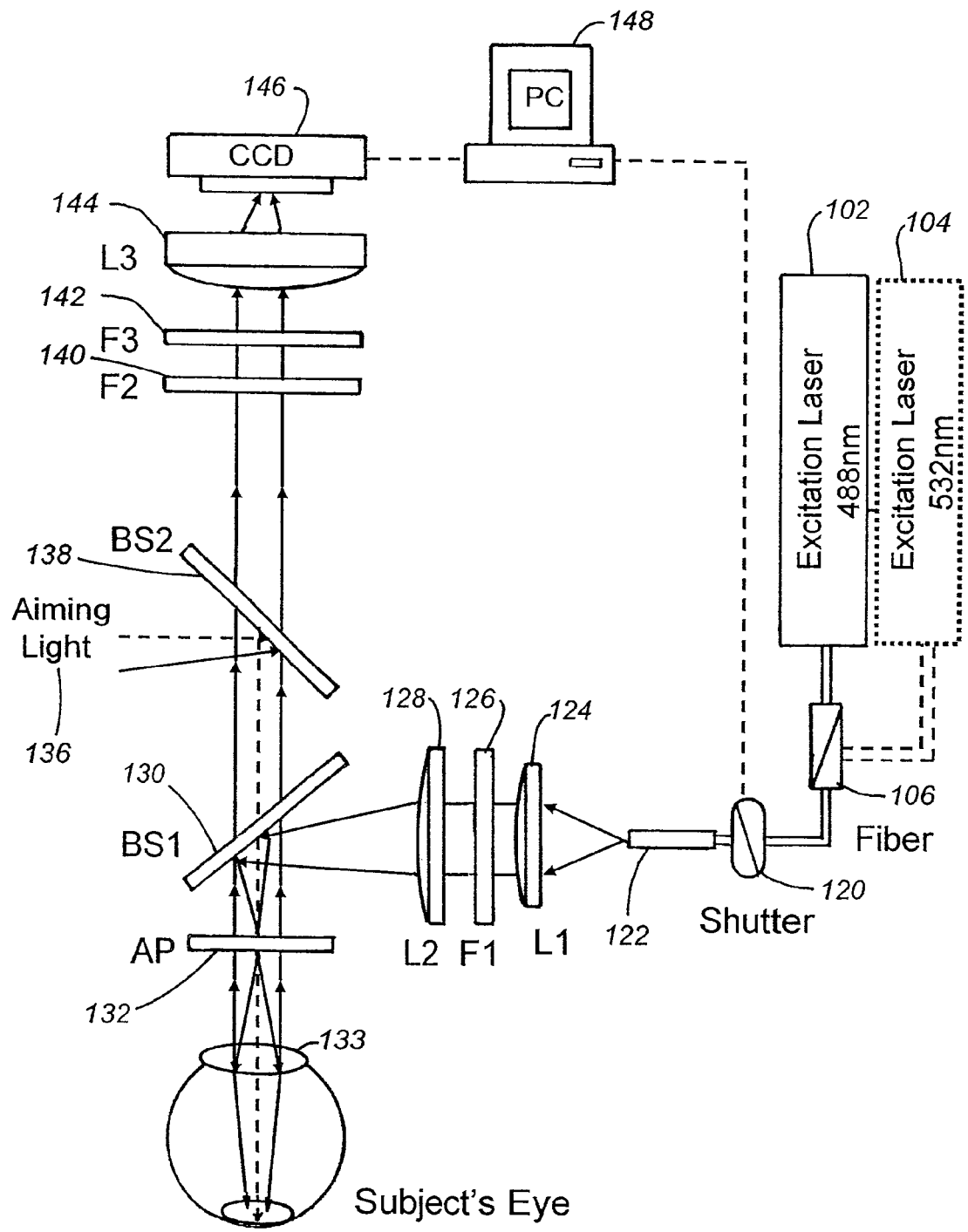
FIG. 4 illustrates schematics of an apparatus used for imaging MP distributions in living human subjects according to the invention.

An example of an inventive apparatus 100 where it can be employed for measuring macular pigments using autofluorescence spectroscopy, is schematically depicted in FIG. 4. This system is configured for obtaining MP measurements by direct, large diameter, laser or non-laser light excitation of a foveal and peripheral macular area, spectrally isolating the captured fluorescence, and using an imaging CCD camera for fluorescence detection. As described below, the system is designed to maximize the throughput for fluorescence originating from the retina.

The depicted apparatus 100 includes a light source(s) that emits light at a wavelength or wavelength range that overlaps the absorption band of both macular carotenoids and the absorption band of lipofuscin, for example a first coherent, or non-coherent conventional light source 102 and an optional second coherent light source 104, for example 488 nm and 532 nm fiber-coupled solid state lasers. Alternatively, light sources 102 and 104 may comprise other devices, such as light emitting diodes (LEDs) for generating nearly monochromatic light, or suitably filtered, i.e. spectrally narrowed, conventional light sources. It is because of the other inventive aspects of the system and methods described herein that relatively low power and low cost LEDs can be used.

The light sources 102 and 104 are in optical communication with one or more light delivery optical components, which direct laser light to the macular tissue to be measured. The laser beams are combined in an optical beam combining cube 106, sent into an optical fiber 122, expanded at the output end of fiber 122 with an achromatic lens 124, and filtered by a narrow-band interference filter 126. The light is then projected onto the retina using focusing lens 128, a dichroic holographic beam splitter 30 and the combination of the human cornea and eye lens 133 (eye lens is not shown). The resulting excitation disk on the retina is preferably about 3.5 mm in diameter. The excitation disk has an intermediate focus at the position of an aperture 132 that is positioned in front of the eye (about 1 cm distance), and that effectively blocks spurious reflections originating from beam splitter 130.

To ensure steady fixation of the eye during measurements, a red aiming laser 136 is used as the fixation target. It is routed into the setup with an uncoated quartz beam splitter 138. The fixation light is directed either to the fovea, for measurements centered on the fovea of the macular region, or to the peripheral macula (about 7 degrees eccentricity). The fixation laser beam diameter on the retina is about 200 microns. The optical shutter 120 is designed such that it transmits a small portion of the excitation light even when it is closed. This allows the subject to view both the red fixation target and the superimposed laser excitation disk for optimum head alignment, which is further facilitated by an adjustable chin rest.

At prolonged viewing, the leaked excitation light (6.9 log trolands) effectively bleaches more than 90% of the photoreceptor pigments of the macula. This establishes uniform background absorption throughout the exposed retina.

The lipofuscin fluorescence is captured by one or more light collection optical components, which direct laser light to the macular tissue to be measured. As depicted in FIG. 4, light is thus routed back through beam splitter 130, which is transparent for wavelengths above about 580 nm, through holographic notch filter 140, which blocks excitation light wavelengths, and through a long-pass filter, 142, which is transmissive above 700 nm. Limitation of the fluorescence to wavelengths above 700 nm insures rejection of light from unwanted fluorophores like the lens, and provides optimum contrast between peripheral and macular fluorescence intensities, as shown below.

The light beam delivery system is in optical communication with a an optical detector such as a light detection system 146, that is used to measure the intensity of the scattered light over the target area of interest. The light detection system 146 may include, but is not limited to, devices such as a CCD (charge coupled device) camera or detector array, an intensified CCD detector array, a photomultiplier apparatus, photodiodes, or the like. For example, the light can be collected by a 50 mm focal length achromat 144 and imaged onto the pixel array of a CCD camera (e.g. a 512.times.512 pixel array of a CCD camera Model ST-9 XE, available from the Santa Barbara Instrument Group, Inc.). For the Model ST-9 XE camera, individual pixel dimensions are 20 micron height by 20 micron width; quantum efficiency in the red/near IR drops slowly from 60% at 650 nm to 40% at 800.

The detected light is converted by light detection system 146 into an electronic signal, typically processed by software associated with the detection system, and sent to a computing device such as a microprocessor or personal computer 142 or the like. The computer 148 can control the shutter 120 as well. For data analysis, the pixel intensity maps can be converted to proportional files, and further processed using suitable image processing software (available, e.g. from The MathWorks, Inc.).

The signal is then analyzed and visually displayed on the monitor of computer 148. It should be understood that the light detection system 146 may also convert the light signal into other digital or numerical formats, if desired. The resultant signal intensities may be calibrated by comparison with chemically measured carotenoid levels from other experiments. The computer 148 preferably has data acquisition software installed that is capable of spectral manipulations.

During operation of apparatus 100, laser excitation light from either light source 102 or 104 is routed via optical beam combining cube 106, mechanical shutter 120, optical fiber 122, and dichroic beam splitter 130 to the retina of the eye to be measured. The lenses 124 and 128 image the output face of the optical fiber delivering the laser excitation light onto the retina of the eye to be measured. The notch filter 126 transmits only the laser excitation light. The lipofuscin emission from the retina of the measured eye is transmitted by dichroic beam splitters 130 and 138 and detected by light detection system, 146 such as a CCD camera, after traversing filter 140, 142 and lens 144. A red aiming light 136, serving as a fixation target during the measurement, is projected onto the retina of the eye via dichroic beam splitter 138. The pass filter 142 transmits only the long-wavelength emission of lipofuscin (e.g., at wavelengths larger than about 700). The light detection system 146 then converts the signal into a form suitable for visual display such as on a computer monitor or the like. For example, spatial digital MP images of a subject are recorded by detecting the lipofuscin fluorescence of the retinal pigment epithelium in its long-wavelength emission range upon sequential excitation with 488 nm and 532 nm light, and the spatial extent of MP and its topographic concentration distribution is obtained by digital image processing according to equation (8), which under these wavelength conditions reduces to equation (10), shown below.

Preferably, apparatus 100 is operated on a living mammal, preferable a person, with undilated eyes in a darkened room.

Background noise levels can be in the range of 100 counts per pixel; signal counts typically about 30,000 counts per pixel. The CCD camera temperature is preferably kept uniform, for example at a temperature at or below 5° C. during measurements.

Figure 5:
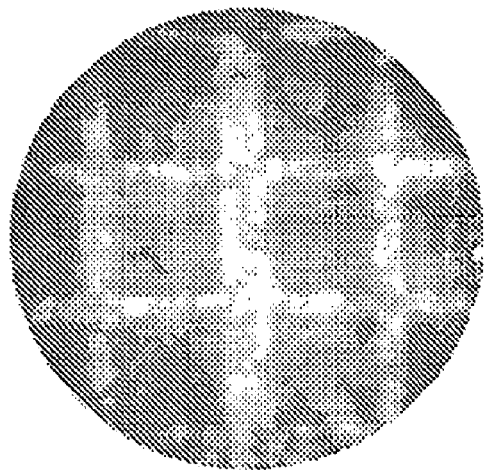
FIG. 5 illustrates the removal of laser speckle effects in fluorescence imaging.
Figure 5:
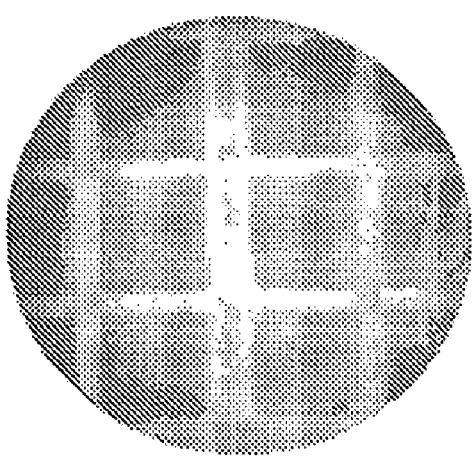
Figure 5:
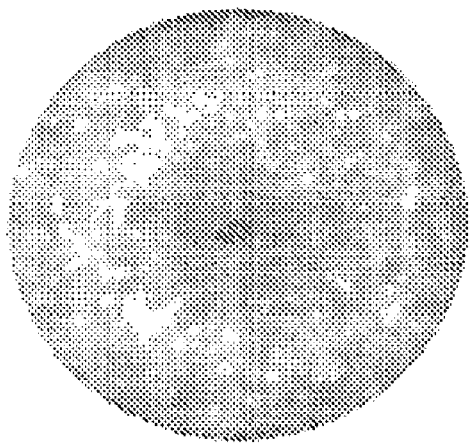
Figure 5:
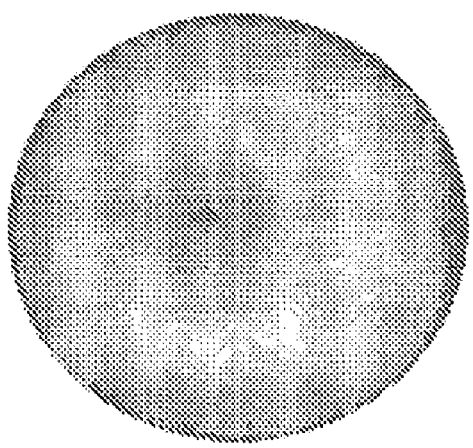

Laser speckle in the images obtained when using coherent laser light as excitation sources can be effectively removed by mechanically shaking the light delivery fiber during measurements, which generates a spatially homogeneous laser excitation spot via fiber mode mixing. The resulting speckle removal effect and its impact on the obtainable image quality is illustrated in FIG. 5 for images of millimeter graph paper, (a) to (b), and the macular area of a human retina (c) to (d), respectively, demonstrating that fine details such as small retinal blood vessels in the peripheral macula can be resolved after speckle removal. Since a 1 mm distance is imaged onto a pixel array distance of 120 pixels, the invention provides about a 10 micron spatial resolution under the used imaging conditions after speckle removal. Speckle removal procedures will not be necessary if incoherent, non-laser light excitation sources are used.

Figure 6:
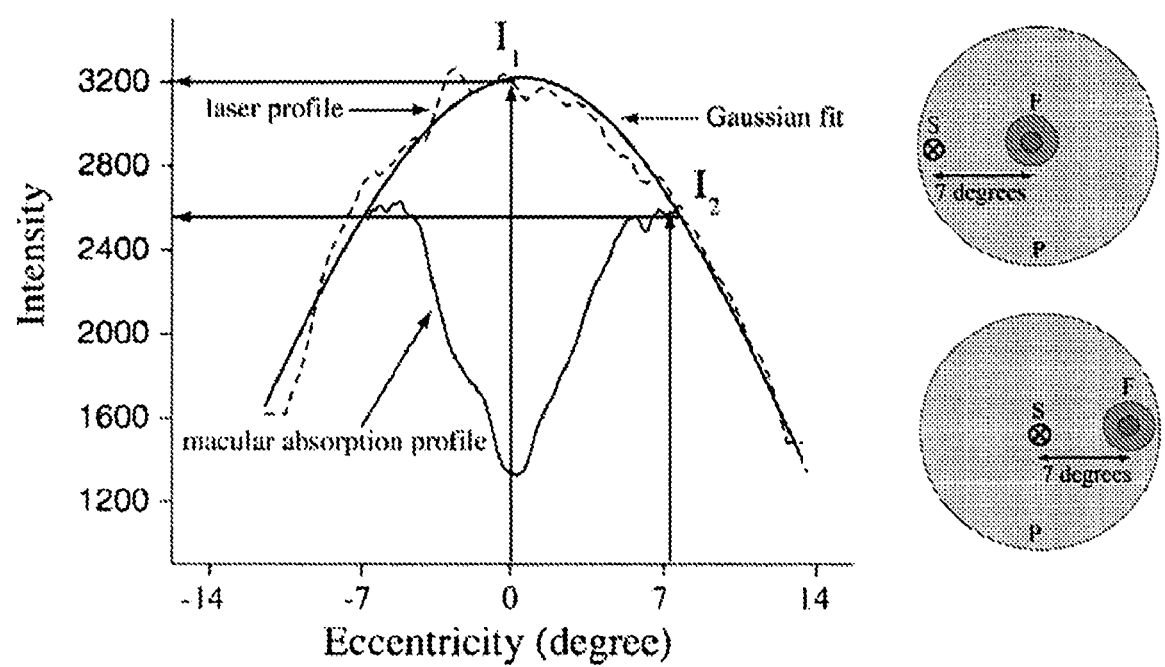
FIG. 6 illustrates the determination of a spatial correction factor for image processing due to spatially varying intensity profiles in laser excitation and lipofuscin fluorescence disks.

For correct imaging of large tissue regions, and for the purpose of comparing MP measurements for single-wavelength (488 nm) and dual-wavelength (488 and 532 nm) measurements, intensity corrections have to be made that account for intensity variations of the typically Gaussian shaped laser beam profile and the resulting fluorescence response across the excitation spot. To illustrate this point, the lipofuscin distribution in the peripheral macula and in the foveal area was imaged using an approximately 3.5 mm diameter light excitation disk. As seen from FIG. 6, the measured lipofuscin intensity distribution, which is shown as dashed curve, follows again a Gaussian beam profile, dropping for both wavelengths (488 and 532 nm) by about 20% from the central intensity level to reduced level at the periphery of the fluorescence image. Thus, fluorescence intensity levels at the edge of the image disk have to be multiplied by a corresponding correction factor (about 25%) before comparing them with central image values.

To eliminate the potential for any deviations from these profiles in living human eyes due to scattering and absorption effects of the anterior ocular media, the lipofuscin distribution of the retina was imaged in two specific locations. As sketched in FIG. 6, one of the two images is centered on the fovea. It is recorded for this centrally fixated subject such that a 7-degree eccentric location, termed S, is recorded along with the fovea, F. Subsequently, a second image is recorded which is now centered on the same peripheral location S, achieved by having the subject fixate on the aiming laser that has been changed in direction by 7 degrees. Since the spot S has an unchanging lipofuscin concentration, any detected difference in fluorescence intensities originating from the spot S in the two images has to be due to the laser excitation intensity beam profile plus the combination of scattering and absorption effects of anterior ocular media. Comparing the corresponding intensities of the two images, in view of the disclosure herein one can derive a spatial correction factor map for each subject.

In a preferred aspect of the invention, laser power levels at the cornea can be 2 mW during measurements with exposure times of 200 msec. At a retinal excitation disk size of 3.5 mm diameter, the light exposure was thus about 3 mJ/cm$^2$, which is approximately a factor of 3 below the photothermal safety limit of 10 mJ/cm$^2$ set forth by the ANSI standard. The photochemical limit for retinal injury is listed in the same standard as 15.5 J/cm$^2$ for the used wavelengths. At the used energy density of 3 mJ/cm$^2$, the exposure is therefore a factor of about 5,000 below the photochemical limit. Accordingly, exposures suitable for use in the invention are preferably less than about 10 mJ/cm$^2$, more preferably less than about 5 mJ/cm$^2$, still more preferably less than about 3 mJ/cm$^2$. Exposure times are preferably less than about 1 second, more preferably less than about 500 msec, still more preferably less than about 200 msec. In fact, and as mentioned elsewhere herein, such low levels can be used with the methods and apparatus of the invention that light emitting diodes can substitute for lasers in some embodiments.

Figure 7:
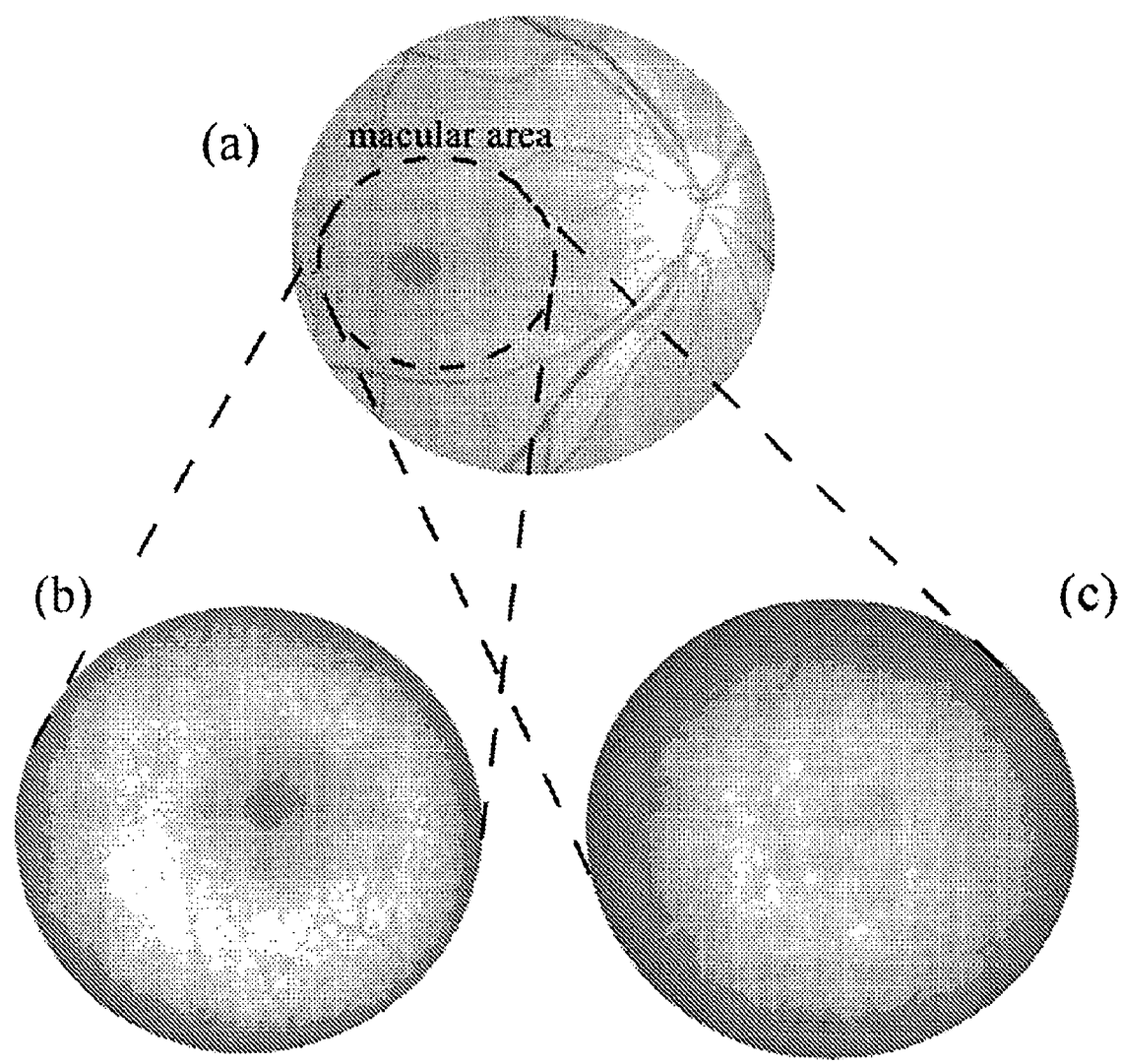
FIG. 7 is a white-light fundus camera image of a healthy subject (image a), and lipofuscin fluorescence images of the fundus obtained at near infrared wavelengths with 488 nm (image b) and 532 nm (image c) laser excitation, respectively.

FIG. 7 includes photomicrographs of the macular region of the retina of a human volunteer subject. Image a is an image obtained by measuring the reflection of white light (standard fundus image). Images b and c are typical retinal lipofuscin fluorescence images, or pixel intensity maps, with image b showing a lipofuscin fluorescence digital fundus image obtained under 488 nm excitation and image c showing a lipofuscin fluorescence digital fundus image obtained under 532 nm excitation, each obtained at near IR wavelengths ($\lambda$<700 nm). The field of view for image a is larger than for images b and c in order to illustrate the relative location of the macular region (gray shaded area on left side of image a) with respect to the optic nerve disk (bright white spot on right side of image a). Images b and c are centered on the macular region and are recorded, respectively, with 488 nm light that is absorbed by both lipofuscin and macular pigments, and with 532 nm light that falls outside the absorption range of macular pigments, and therefore only weakly excites the lipofuscin emission.

The two images b and c differ substantially in the macular region, showing pronounced absorption due to MP under 488 nm light, and virtually no absorption under 532 nm light excitation, as expected from the MP absorption behavior (see FIG. 1).

Small blood vessel patterns in these images can be used as landmarks to align these two distributions for digital image processing. A digital subtraction image due only to the MP absorption can be obtained by subtracting image c from image b. For example, the spatial extent of MP and its topographic concentration distribution can be obtained by digitally subtracting image c, serving as a reference pixel intensity map, from image b, which has pixel areas with reduced intensities due to absorption of the lipofuscin emission by MP (central shaded area).

Particularly, the lipofuscin fluorescence intensity map obtained under 532 nm excitation can be used to assess the distribution of the lipofuscin and melanin concentration throughout the retinal area of interest, i.e. the area centered on the fovea and subtending to about 7 degrees or higher eccentricity. This is the case since the $I_{532}$ intensities decrease from the macular image location with $I_{max,532}$ to the peripheral location with $I_{min,532}$ only by the known correction factor, $c_{Gauss}$ (this factor is described above and is due to the combined Gaussian laser excitation and fluorescence response profile).

Next, in order to derive the MP optical density in the fovea or surrounding regions, The invention use the measured lipofuscin fluorescence intensity maps obtained under 488 nm and 532 nm excitation, respectively, to determine the MP optical density difference from equation (9), which becomes $$O.D. = 1.2 \times \left[ \log\left(\frac{I_{max}}{I_{min}}\right)_{\lambda=488} - \log\left(\frac{I_{max}}{I_{min}}\right)_{\lambda=532} \right], \quad \text{(Eq. 10)}$$

where $I_{max}$ and $I_{min}$ are intensities averaged over certain pixel areas (see below). The factor 1.2 takes into account the ratio between the absorption of MP at its maximum (460 nm) and the used excitation wavelengths of 488 nm and 532 nm. The invention determined this factor from the absorption spectrum of MP measured from an excised eye cup.

Figure 8:
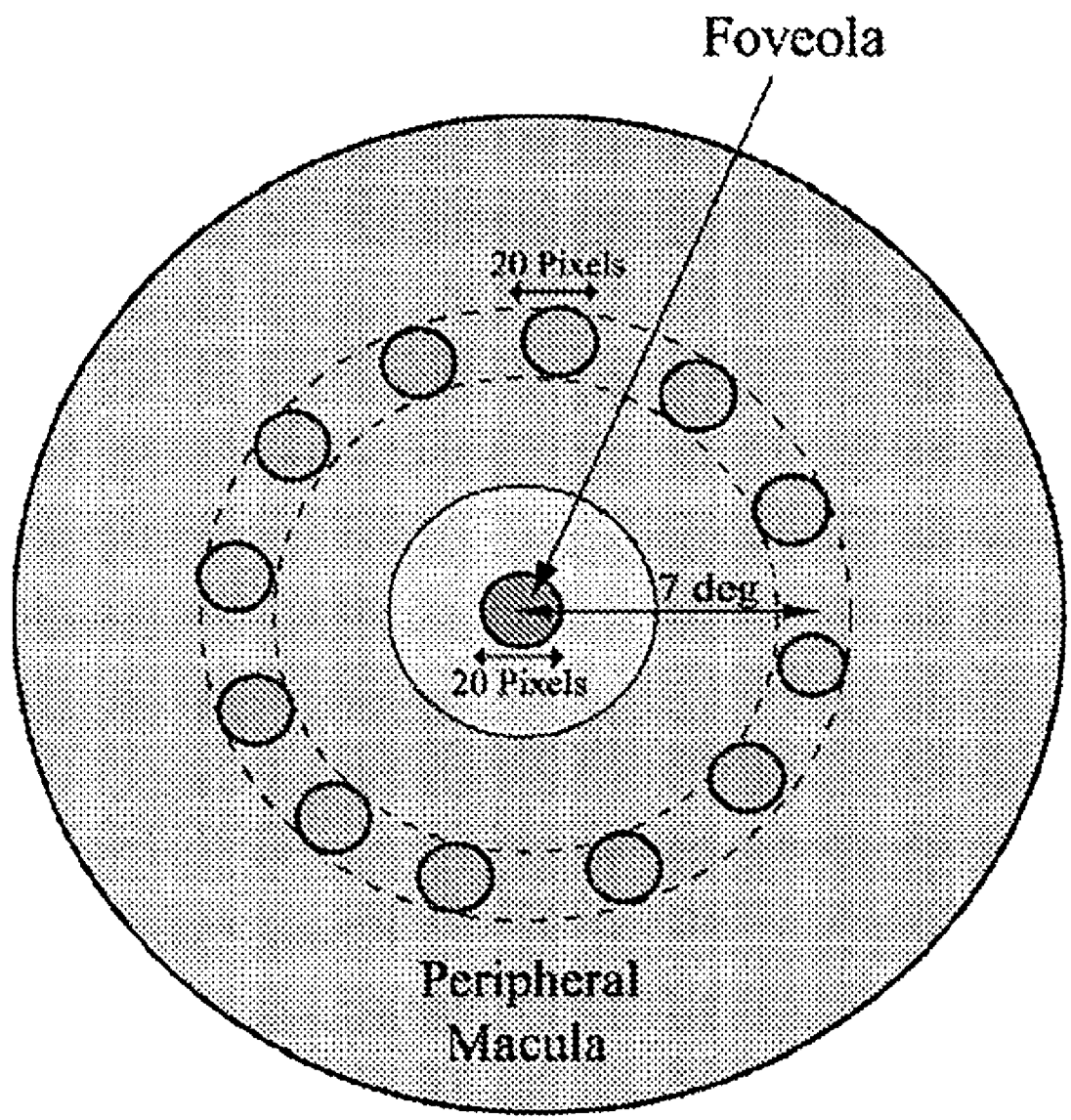
FIG. 8 illustrates schematics showing processing of CCD pixel intensity regions to derive optical density values of MP absorption at any desired location in the retina.

FIG. 8 illustrates schematics showing processing of specific CCD pixel intensity regions chosen to derive optical density values of MP absorption at any desired location in the retina. By way of example, for the calculation of average MP levels in specific locations or along nasal-temporal and inferior-superior meridians, individual pixels can be grouped into disks with a diameter of 20 pixels, as illustrated in FIG. 8. Averaged peripheral pixel intensities are determined from twelve peripheral pixel disks located on a circle with 7 degrees eccentricity to the fovea, and the average pixel intensity in an area of interest is determined from an additional, single, disk positioned in that area, for example in the fovea, as shown in FIG. 8. One central disk is located at the center of the macula, the foveola, with a resulting intensity $I_{min}$ (ave). Twelve additional discs are chosen on a circle with 7 degrees eccentricity to the foveola, with equidistant spacing, to calculate an average fluorescence intensity $I_{max}$ (ave) in the periphery. The maximum MP image contrast, derived from these two averaged intensities, is proportional to the optical density of MP in the center of the macula, according to equation (8) or (10). Disks in between the center and the peripheral circle (not shown) can be chosen to calculate the image contrast and MP at any eccentricity toward the peripheral retina.

In measurements of dozens of healthy subjects it was seen that images recorded with 532 nm excitation contributed only 5% change to the MP levels obtained from imaged recorded with 488 nm excitation alone. In a preferred embodiment a single wavelength, 488 nm laser exposure is therefore adequate to determine the MP levels with high (about 95%) accuracy, and for most practical purposes it is therefore not necessary to use an additional second excitation wavelength outside the MP absorption range for MP level determinations.

However, in the presence of macular pathology, it is very likely that dual wavelength measurements will be necessary to account for spatially non-uniform lipofuscin and melanin distributions. The fluorescence based MP detection method, as carried out in this invention, shows a statistically significant correlation with MP measurements using highly MP specific Resonance Raman spectroscopy in healthy subjects, as seen from a direct comparison of both techniques in a subgroup of 48 subjects. MP levels showed a tight correlation up to integrated MP optical density levels of about 0.35. At higher MP levels, deviations occur that are likely correlated to nonlinear effects of both optical methods at higher MP levels. Possible factors include (a) screening effects in the MP Raman and lipofuscin fluorescence responses at high molecule concentrations, (b) an under-sampling of the MP distributions caused by lens opacity effects in elderly subjects in the Raman method, (c) non-vanishing MP levels at the peripheral retinal reference point in the fluorescence based method, and (d) residual absorption of photoreceptors in the fluorescence detection. The invention expects further insight into the differences between both methods by a direct comparison of fluorescence based imaging results with Raman images of MP distributions in the same subjects.

The invention can be used in a variety of contexts to benefit subjects. For example, correlative studies can be performed using spatial imaging of MP concentrations with changes over time or particular shapes (See FIGS. 14 and 16) to correlate MP levels with pathologies, and potential increases occurring upon dietary interventions and supplementation. Particularly, either 3d patterns or observed changes with aging may be indicative of certain diseases. In a preferred aspect of the invention, the measured MP data can be used to proscribe a treatment, vitamins, dietary supplements, etc. to a subject. Because the test can be performed in under a second using low light power, even LEDs in some instances, and in non-mydriatic conditions, the test is ideal for rapid and proscribed or elective testing in a variety of environments, from doctors offices and hospitals to less formal setting such as optometry shops and dietary supplement stores. The data obtained from a test can be used to customize treatment plans and counteract health problems.

The following examples are given to illustrate the present invention, and are not intended to limit the scope of the invention.

EXAMPLES

Example 1

For the determination of the MP optical density, the obtained image contrast is important, being directly proportional to the MP optical density. In living eyes, care must be taken that the lipofuscin fluorescence image contrast is not artifactually reduced or enhanced by other absorbing or fluorescing compounds besides MP. For example, if an artifactual fluorescence signal existed in the macula, it would add to the fluorescence level of lipofuscin, and thus reduce the image contrast. Likewise, an extra fluorescence signal in the periphery, or an absorption in the center from unbleached photoreceptors, would enhance the image contrast. A presence of artifacts would be obvious if there were to be a wavelength dependence of the obtained image contrast, i.e. if the image contrast were to change depending on which spectral portions of the lipofuscin fluorescence were included in the measurement and subsequent derivation of the MP levels.

Figure 10:
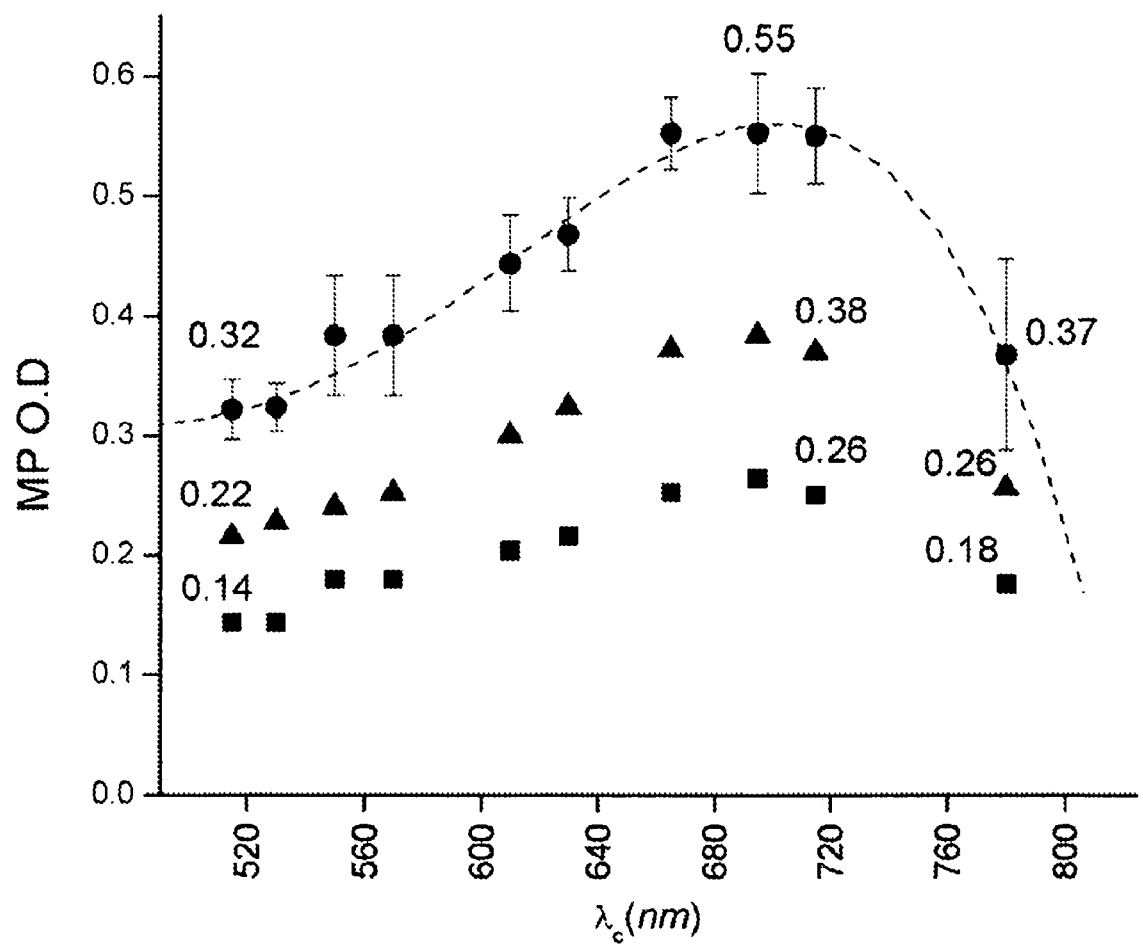
FIG. 10 illustrates the wavelength dependence of MP optical density obtained when successively limiting the detected fluorescence range to longer wavelength, using long-wavelength pass filters with suitable cut-on wavelengths, $\lambda c$.

With reference therefore to FIG. 10, in order to check for the existence of artifacts, a series of measurements were carried out in which the detected lipofuscin fluorescence signals were limited to progressively longer wavelength regions. Using long-wavelength step function transmission filters with successively longer cut-on wavelengths with the two-wavelength measuring scheme (488 and 532 nm), and testing the effect on three subjects, the MP results shown in FIG. 10 were obtained. The optical density values were computed with equation (10), and included correction of the respective digital images for laser intensity variations within the excitation disk ($c_{Gauss}$). Enhancement factors of 1.71, 1.72, and 1.85 were observed, respectively, of the image contrast at wavelengths limited to 700 nm and beyond, as compared to MP levels obtained when including fluorescence components in the blue-green spectral region. The variability of the results in FIG. 10 did not correlate with the age of the subjects.

Example 2

To test whether the interfering green fluorescence component originates from intrinsic MP fluorescence (see FIG. 1 for the emission spectrum), an excised eye cup was imaged from a donor eye, using essentially the same imaging setup as for living eyes an MP O.D. value of about 0.4.+−.10% was obtained for this sample throughout the wavelength range 530-700 nm, thus revealing an absence of a wavelength effect on the optical density. This proves that intrinsic MP fluorescence is too weak to interfere with the obtainable image contrast of the lipofuscin fluorescence based imaging technique.

Example 3

Next, the wavelength dependence for the foveal MP levels of a subject having an implanted, non-fluorescing prosthetic eye lens was measured. Again, an absence of a wavelength effect over the range 530-700 nm was observed. From these results it is seen that the artifactual green fluorescence present in living eyes originates from fluorophores present in the living eye lens. For the purpose of obtaining optimum image contrast and corresponding MP level determination, according to the invention it is important to detect fluorescence levels only on the long wavelength shoulder of the lipofuscin fluorescence, i.e. above about 700 nm.

Example 4

In order to test the setup in FIG. 4 and the image processing routines, a tissue phantom was imaged in exactly the same geometry and under the same conditions as used for living eye measurements (180 degree detection geometry with CCD camera detection), including identical light filtering and pixel processing routines. The tissue phantom consisted of a dried drop of lutein solution spotted onto one of the side windows of a thin-walled cuvette filled with a methanolic A2E solution, as illustrated in FIGS. 9a and 9b. The optical density of the solution had a value of 0.35 at 488 nm. The dried lutein spot was roughly circular in diameter (about 2.5 mm), and had a non-uniform thickness and concentration that increased from the center on outwards. Using a small diameter (200 μm) 488 nm laser excitation spot, the lipofuscin fluorescence intensity of the lutein spot/A2E solution combination, or the A2E solution alone, was imaged progressing from the center of the lutein spot toward the periphery and beyond. Simultaneously, the in-situ sample transmissions at the laser wavelength was also measured, using a light chopper in the excitation laser beam, and phase-sensitive detection of the transmitted laser beam with a silicon photo-detector placed behind the tissue phantom. From these measurements lipofuscin-emission based optical densities of local lutein concentrations inside the phantom spot was correlated with optical density values obtained from transmission data. The results are displayed in FIG. 9c for a few dozen locations within the lutein spot. They demonstrate excellent agreement between the two methods (correlation coefficient R=0.96), proving that the imaging procedures and data processing routines lead indeed to the desired lutein optical density determination for this tissue phantom. Transmission based absorption levels had an accuracy of 2%; indirect, lipofuscin based absorption levels an accuracy of 4%.

Examples 5-8

Figure 11:
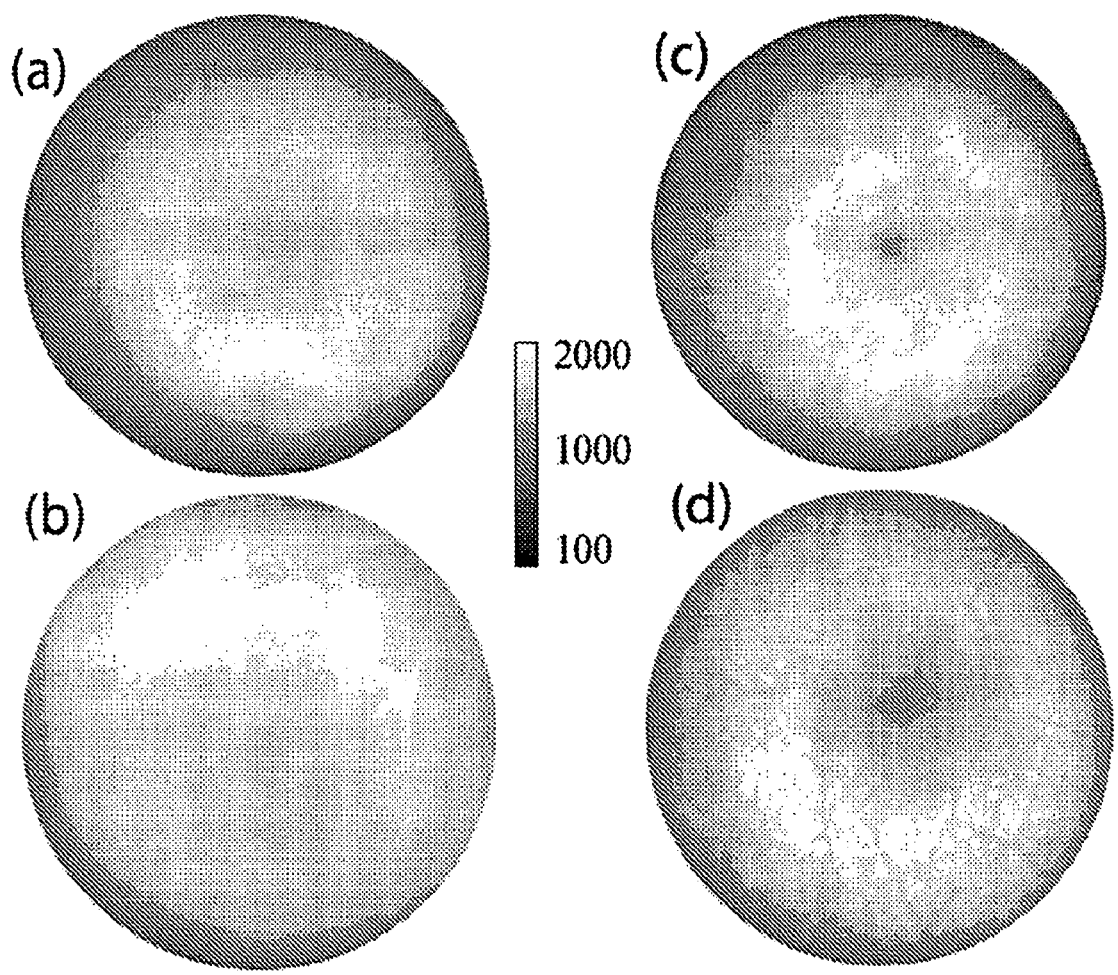
FIG. 11 displays lipofuscin fluorescence images of four volunteer subjects (a-d), obtained under 488 nm excitation, with intensity levels coded in gray scale.
Figure 12:
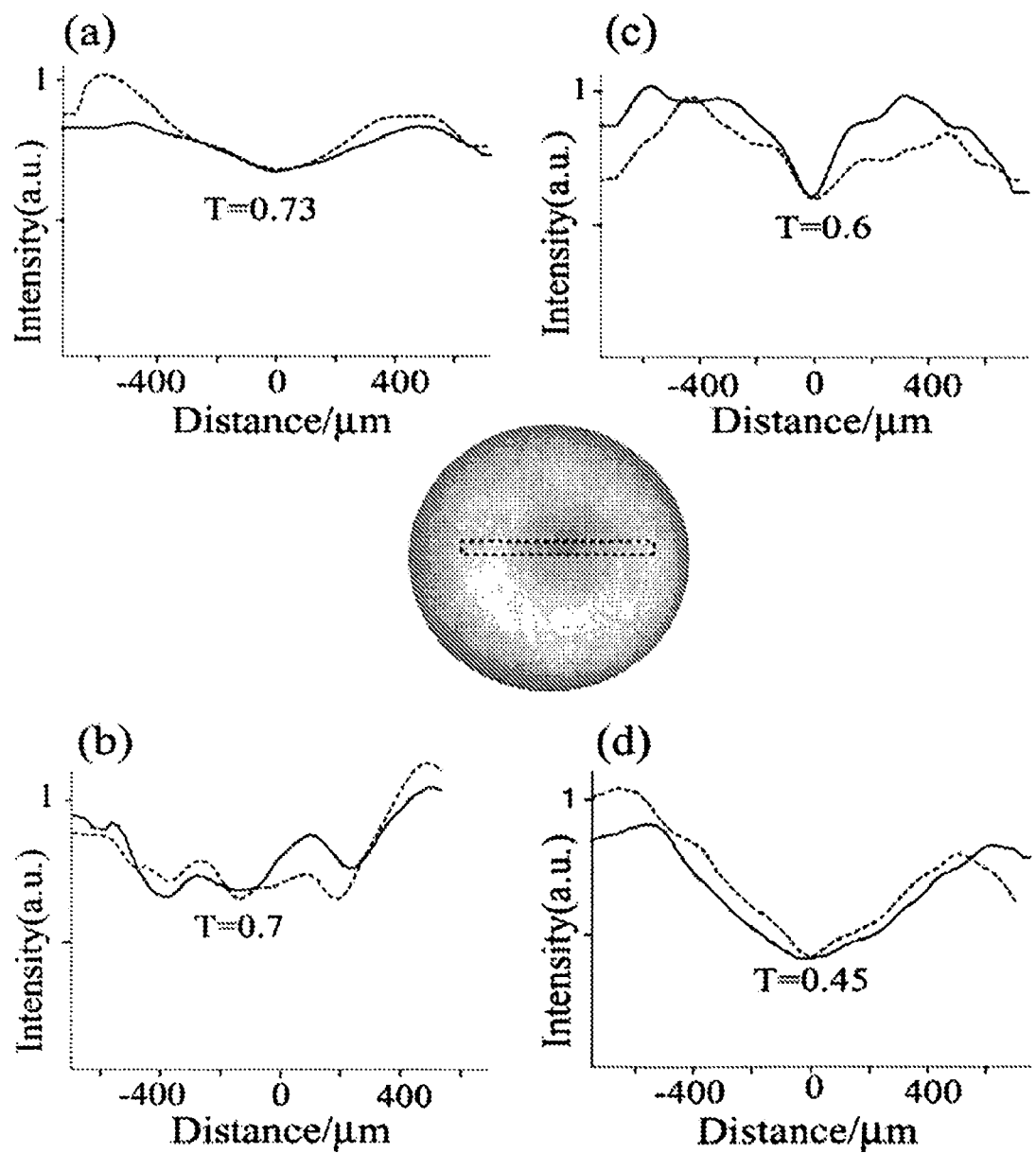
FIG. 12 shows lipofuscin fluorescence intensity profiles, derived from FIG. 11, along nasal-temporal meridans (solid curves) and inferior-superior meridians (dashed curves), all running through the center of the macula (see insert)
Figure 13:
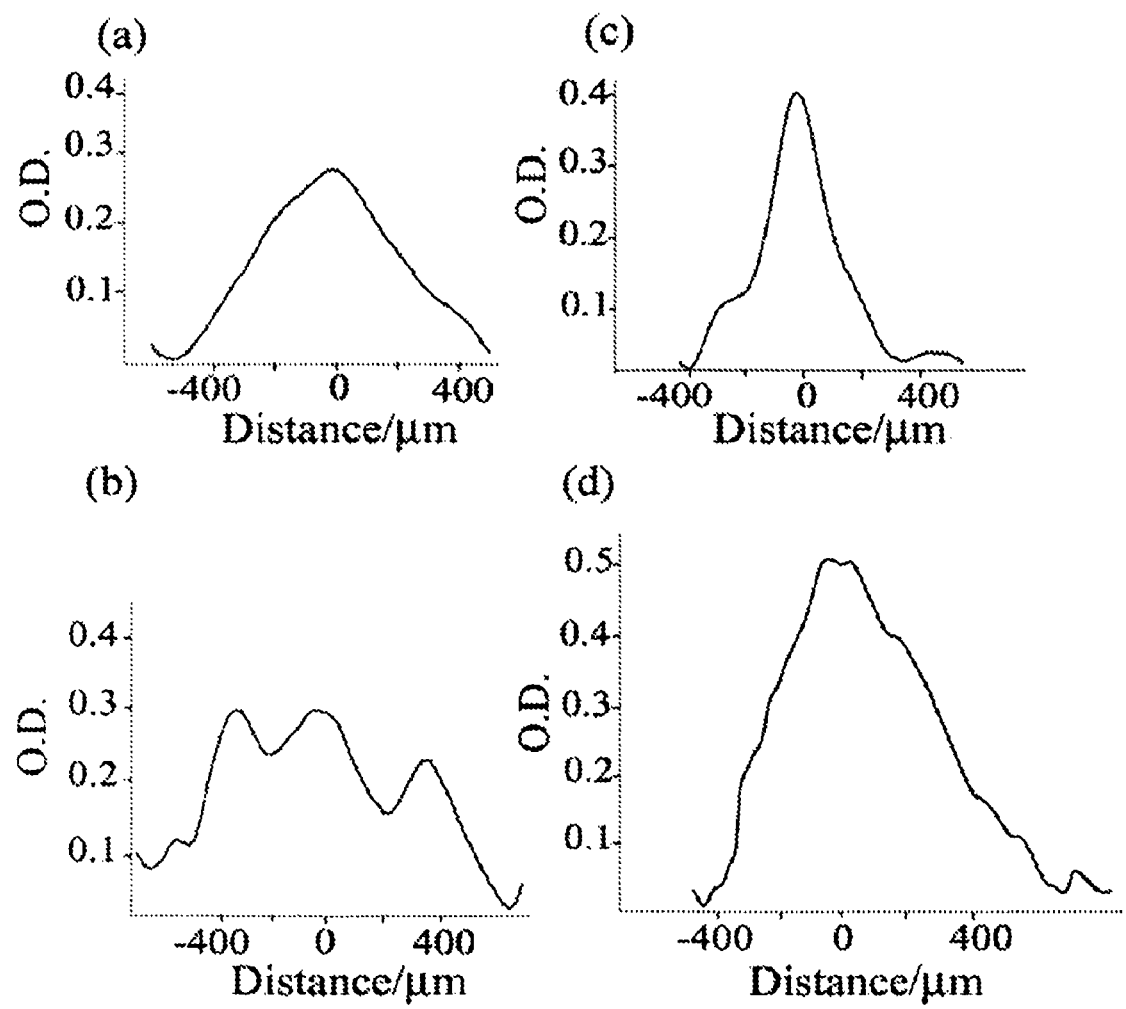
FIG. 13 shows MP optical density plot profiles along the nasal-temporal meridian, derived from FIG. 11 for each subject.

FIG. 11 shows representative MP imaging results for four healthy volunteer subjects, labeled (a)-(d), with the obtained spatial MP distributions displayed as gray-scaled intensity levels with 16-bit accuracy. FIG. 11 is lipofuscin fluorescence images of four volunteer subjects (a-d), obtained under 488 nm excitation, shown in gray scale. Fluorescence intensities are lowest in central dark image regions due to absorption of excitation light by MP. Note pronounced variation of MP distributions regarding strength, symmetry, and spatial extent among individuals. These tests were carried out with 488 and 532 nm imaging and corrected for spatial laser intensity variation over the excitation disk ($c_{Gauss}$). In FIG. 12 intensity line plots are displayed that are derived from the gray-scale images for each subject along nasal-temporal and inferior-superior meridians, both running through the center of the macula, respectively. Plots are derived from pixel intensity maps of FIG. 10 for each of four subjects (a)-(d). A transmission value in the foveola can be calculated from the averaged pixel intensities in the peripheral macula and the foveola. In FIG. 13, the MP optical density data are plotted for each subject along the nasal-temporal meridian. In the line plots of FIGS. 12 and 13, pixel intensities were averaged over 14 pixels (280 .mu.m) oriented perpendicularly to the respective meridians, and transmission values were calculated versus distance from the fovea. For one of the subjects, the MP distribution was imaged eight times over a period of four weeks, showing that the MP optical densities could be determined with a test-retest accuracy (standard deviation) of 2.4%.

Figure 14:
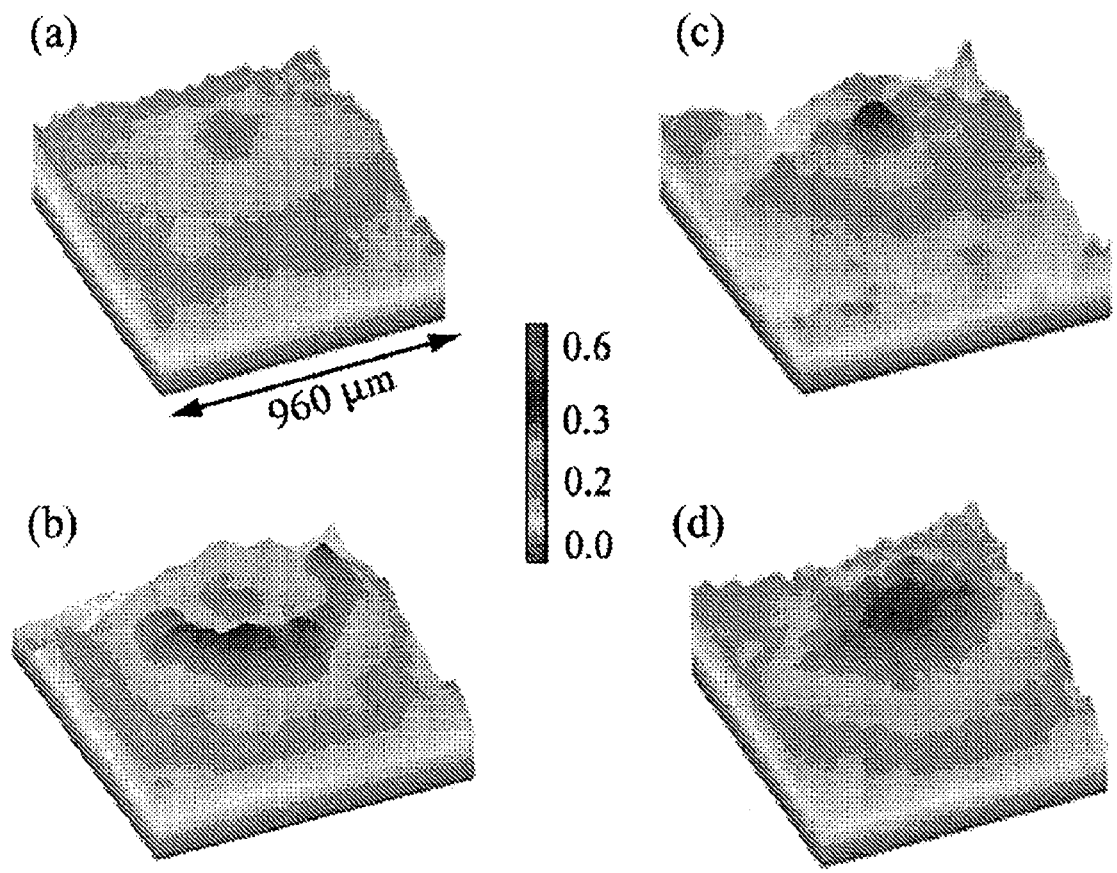
FIG. 14 shows pseudo-color scaled, 3-d, MP distributions derived from the 2-d lipofuscin fluorescence pixel intensity maps of FIG. 11.

FIG. 14 displays pseudo-color scaled, 3-d MP distributions derived from the 2-d gray scaled lipofuscin fluorescence pixel intensity maps of FIG. 8. Note significant inter-subject variations in MP levels, symmetries, and spatial extent.

As can be clearly seen from FIGS. 11-14, the spatial widths, symmetries, and concentrations of MP vary significantly between the four subjects. In subject (a), the MP distribution shows only a weakly enhanced central level compared to the parafovea. In subject (b) the MP distribution has a very low central level and is surrounded by a ring of MP. Subject (c) has a strongly peaked MP distribution in the center, and almost no parafoveal levels and finally, subject (d) has both high central and parafoveal MP levels.

Example 9

To further evaluate the lipofuscin fluorescence-based MP imaging technique, a clinical population study was performed involving 70 healthy volunteer subjects The demographic characteristics of the patient population are shown in Table 1 below. TABLE-US-00001 TABLE 1 Demographics of Population Number of Normal Subjects 70 Age (yrs: mean+/−SD 53+/−16 Age Range (yrs) 23-89 Female (%) 50 Male (%) 50 White Subjects (%) 90 Nonwhite subjects (%) 10 Nonsmokers (%) 86 Active Smokers (%) 14

The MP measurements of the population sample involving 70 healthy subjects reveal distinct patterns of MP distributions, such as a pattern with high central MP levels surrounded by eccentric shoulders or rings of lower MP levels. Also, it is seen that MP levels can differ very strongly among individuals, i.e. by more than an order of magnitude, and that the average MP levels decline slowly with age in the sampled population (on average by a factor of three between age 25 and age 80).

Figure 16A:
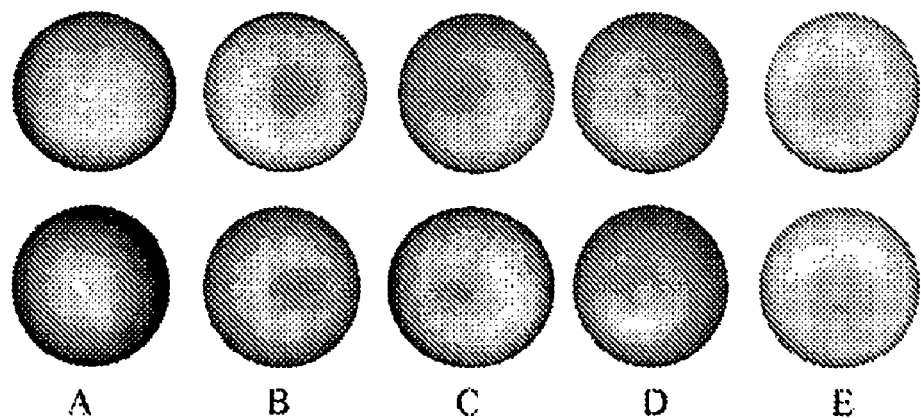
FIG. 16a illustrates categories of MP distributions observed in clinical measurements of 70 subjects (total of 122 eyes)
Figure 16B:
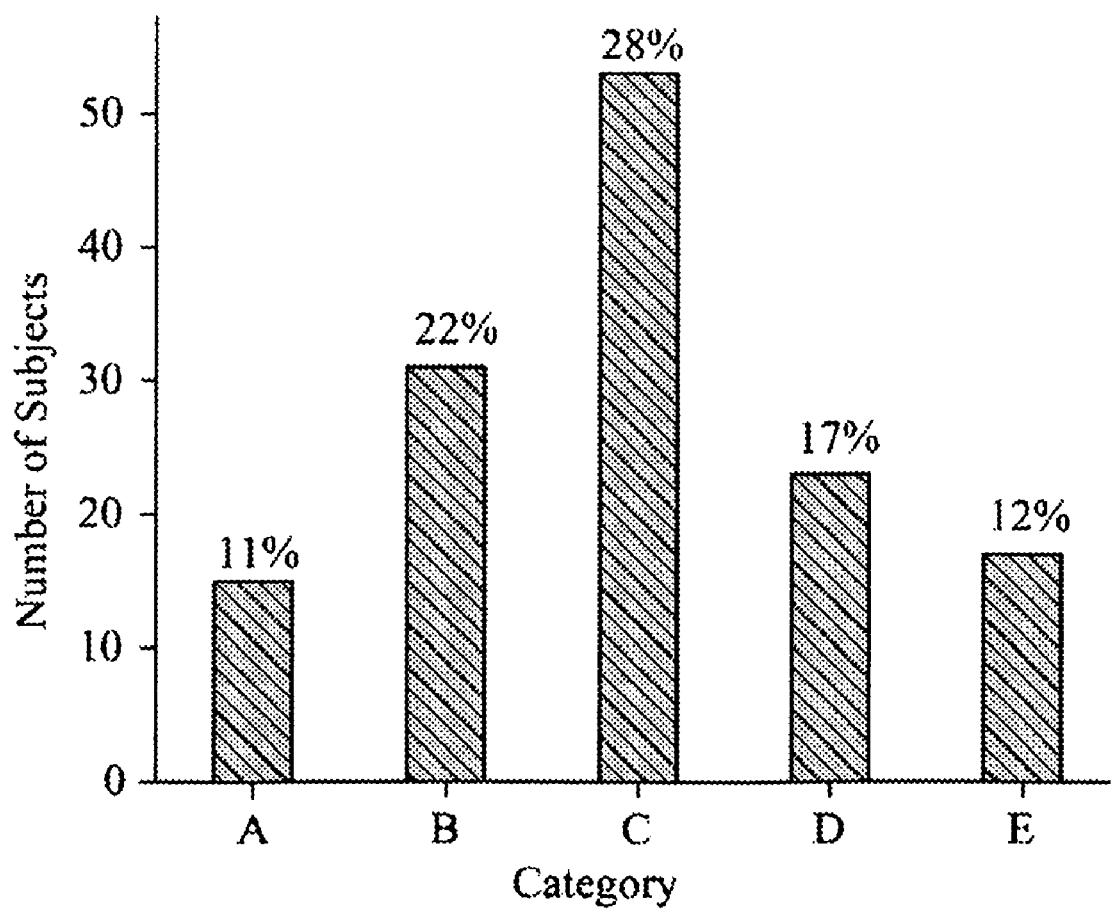
FIG. 16b illustrates the distribution of 122 measured eyes among categories A to E. A large fraction of subjects, 28%, has a sharp, central MP distribution.

FIG. 16 shows distinctive MP distribution patterns observed in these subjects. Five categories, A-E, based on striking spatial features in the MP distributions are depicted at the top of FIG. 16. Two examples are shown for, each category. The bottom of FIG. 16b illustrates the distribution of 122 measured eyes among categories A to E. A large fraction of subjects, 28%, has a sharp, central MP distribution. In category A, MP optical densities were very low (smaller than about 0.05). This is observed for 11% of the population sample. In category B, the MP distribution is laterally extended and has enhanced central MP levels; it is seen in 22% of the subjects. Category C features only a sharp central MP distribution, and is seen in 28% of subjects. Category D has a sharp central MP distribution and an additional MP ring located in the parafovea; this pattern is seen in 17% of the subjects, and has been previously noted by other investigators using autofluorescence and reflectometry. Finally, category E has a relatively uniform, laterally extended, MP distribution with no elevated central MP levels, and is seen in 12% of the subjects.

For twenty of the subjects, the invention recorded images for both 488 nm and 532 nm excitation, and evaluated the MP levels according to equation (10). However, in all subjects an image contrast due to macular MP concentrations was practically absent under 532 nm excitation. The images all looked very similar to that shown in FIG. 7, and contributed at most 5% of the contrast relative to that observed with 488 nm excitation alone. From this, it was concluded that 532 nm images are not essential for MP determinations, at least not in healthy subjects. To facilitate rapid scanning of a clinical population sample, only single wavelength, 488 nm, measurements were used for the remaining subjects. It was also determined, however, that two-wavelength imaging is required to achieve highest accuracies, and it is very likely to be required also for subjects with pathologies.

Figure 17:
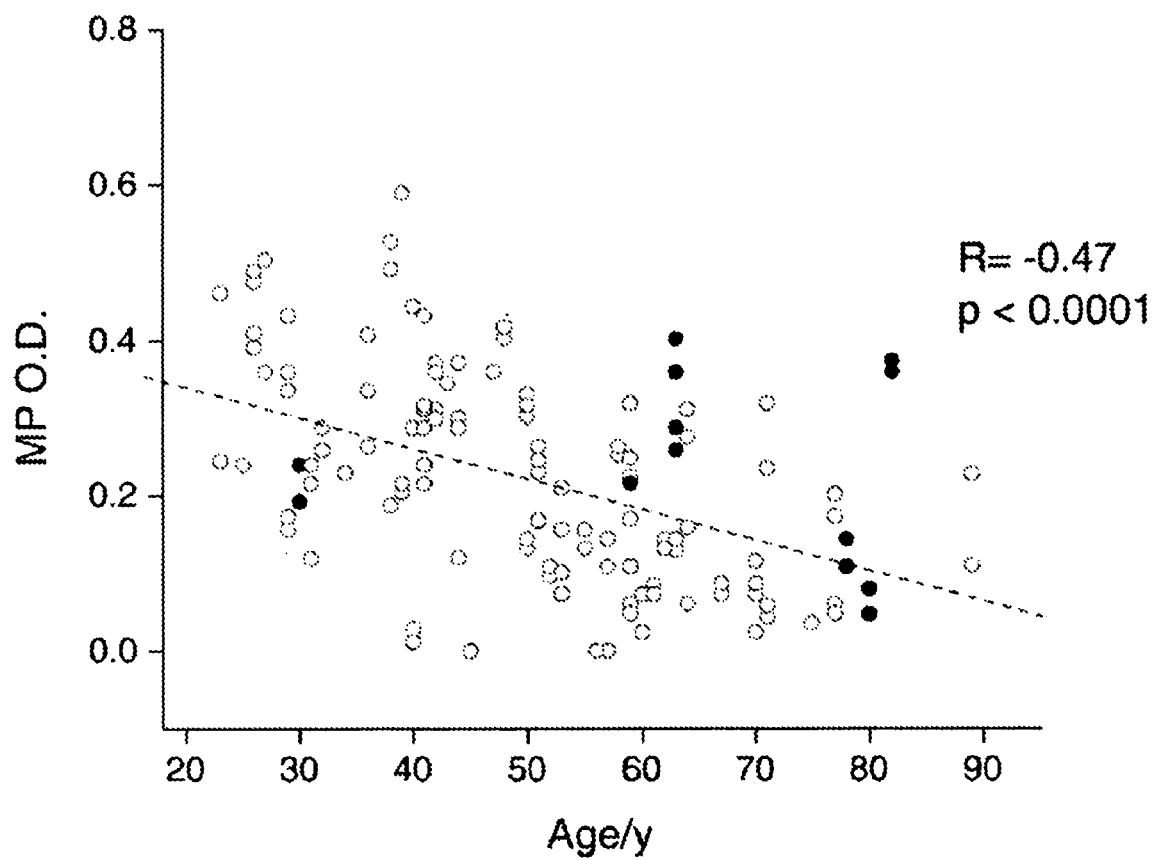
FIG. 17 illustrates the macular pigment levels measured in 90 eyes of a clinical population of 70 volunteer subjects, displayed as a function of age. Each data point corresponds to the maximum MP level determined from lipofuscin fluorescence images.

In FIG. 17 illustrates the macular pigment levels measured in 90 eyes of a clinical population of 70 volunteer subjects, displayed as a function of age. Each data point corresponds to the maximum MP level determined from lipofuscin fluorescence images over its foveolar region (150 .mu.m diameter). Filled circles represent subjects measured after cataract surgery (lens implant). Note the significant variation of MP levels between individuals at any age and the average decline of levels with age. In several subjects with age near 40 years, for example, the MP levels are seen to range from an O.D. near zero to O.D. of about 0.6. Also, there is a statistically significant decline of average MP levels with increasing age; with a correlation coefficient $r=-0.47$. Calculating the correlation coefficient with 1 data point per subject (one eye per subject), $r=-0.54$) was obtained.

Example 10

Figure 18:
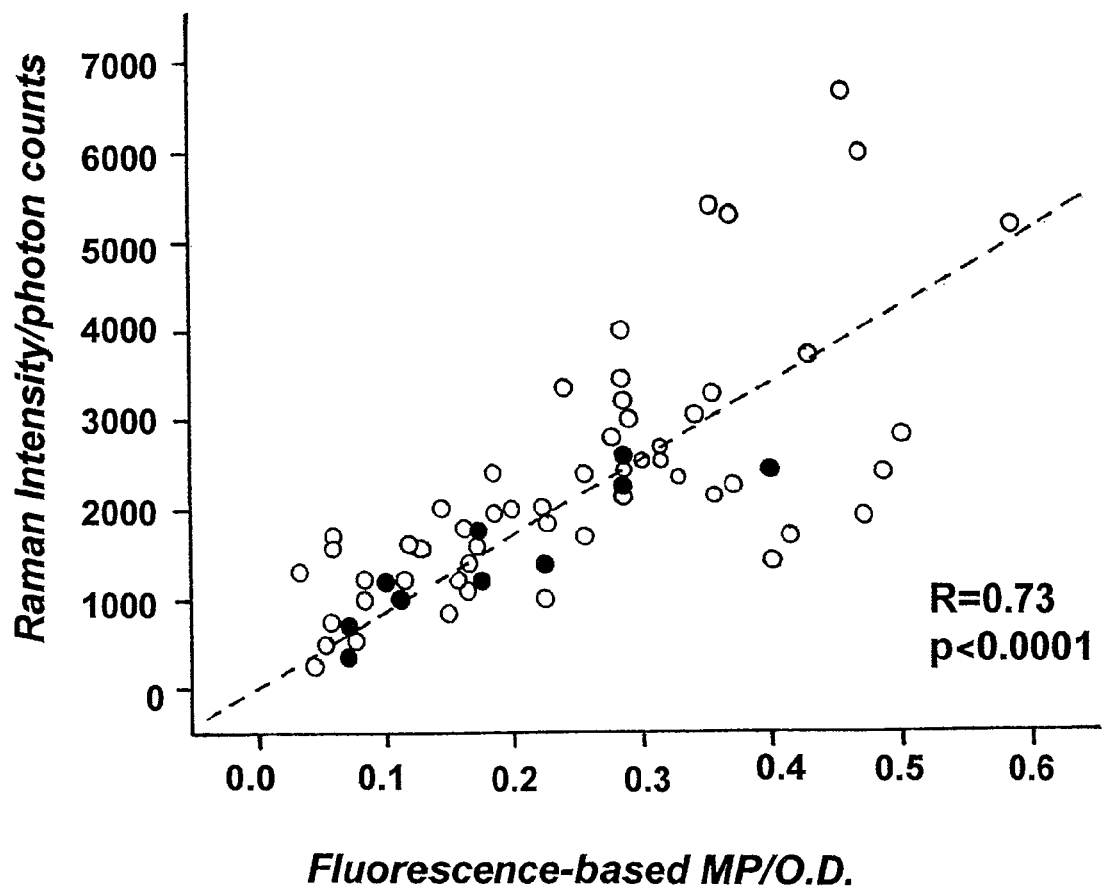
FIG. 18 illustrates the correlation between MP levels determined by lipofuscin fluorescence based imaging and resonance Raman spectroscopy.

The correlation of the indirect, lipofuscin fluorescence-based MP detection technique, was compared with the direct technique of integral Resonance Raman detection, the latter measuring MP responses over an approximately 1.2 mm diameter excitation disk in an integral fashion. For this purpose a clinical population subgroup of 48 subjects was recruited, and 72 eyes were measured. The results are shown in FIG. 18, revealing a statistically significant and strong correlation between both methods (correlation coefficient $r=0.73$, $p<0.0001$ including all eyes measured, and $r=0.75$, $p<0.0001$, including only one eye per subject). The plotted fluorescence based MP optical density levels are maximum levels at the foveola. They are calculated from lipofuscin fluorescence pixel intensity maps integrated and averaged for a circular area, centered at the fovea, having 20 pixel diameter (150 μm). Filled circles in FIG. 18 correspond to data points for subjects with lens implants. Limiting the correlation to MP optical densities below about 0.35, the correlation is even stronger. At optical densities above about 0.35, the variance of the levels increases, likely caused by breakdown of the assumptions underlying the lipofuscin based MP detection method and the resonance Raman methods.

Raman based MP levels are derived from Raman scattered light intensities at the carbon double stretch frequency of 1525 $cm^{-1}$. Since the latter are obtained with a 1 mm diameter, 488 nm laser, excitation spot centered on the macula, Raman based MP levels are averaged over an approximately 1 mm diameter area. Raman based levels are not corrected for media opacities, while fluorescence based levels are not influenced by media opacities. The high correlation therefore demonstrates indirectly that media opacities are not very significant in Raman measurements.

Example 11

Figure 15:
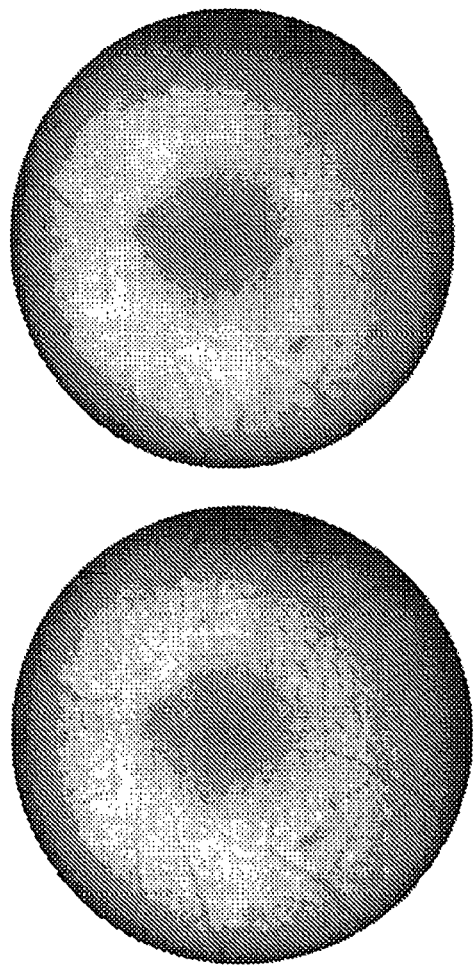
FIG. 15 illustrates the effect of blood vessels on transmission line plots derived from gray-scale lipofuscin fluorescence intensity maps.
Figure 15:
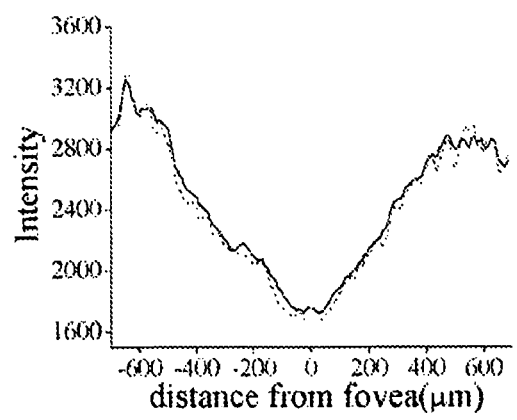
Figure 15:
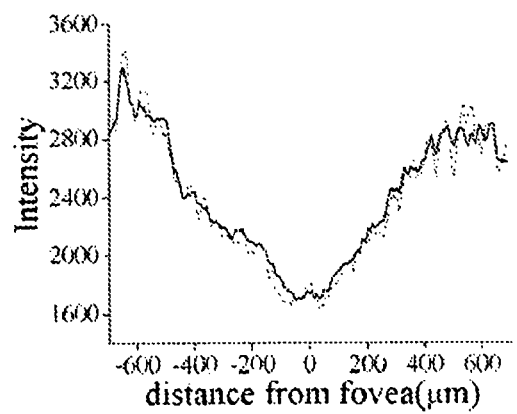

To investigate the influence of blood vessels on the spatial MP asymmetries, the measured pixel intensity maps were processed with reduced vertical pixel averaging, and with software filter masks to enhance finer spatial details. Two gray scale images and corresponding nasal-temporal meridional line plots illustrate the results. They are shown in FIG. 15. In the image shown at the top of FIG. 15, the pixel intensity map is unfiltered. In the image shown at the bottom, the map is filtered and weighted with a Gaussian mask. For both images, resulting transmission line plots are shown resulting from averaging over 15 pixels (solid curves) and 5 pixels (dashed curves), respectively. Averaging of 15 vertical pixels produces smooth curves but reveals pronounced asymmetries in the shoulders of the distribution at about 400 .mu.m eccentricity. Averaging of only 5 pixels, results in a clearly visible spatial fine structure (about 50 .mu.m width) in the shoulders of the MP distribution, as evidenced by large amplitude oscillations in the profile in the about 300-600 .mu.m eccentricity range. The overall spatial asymmetry of the profile, however, is not influenced by the blood vessels. In the higher resolution plots, other spatial details not related to blood vessels are discernible, too, such as the small but clearly resolved dip of the MP absorption profile in the foveola of this subject.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for measuring macular pigment, comprising:
    illuminating the macular and adjacent peripheral retinal tissue of an eye with light at a wavelength that overlaps the absorption band of lipofuscin;
    detecting an intensity of light emission from each of the macula and peripheral retina of the eye at a wavelength range that:
        overlaps the emission wavelength range of lipofuscin; and
        is outside the emission range of interfering fluorophores; and
    determining a topographic distribution of macular pigment in the macular tissue from differing light intensities in both the macula and peripheral retina.

2. The method of claim 1, wherein illuminating the macula and adjacent peripheral retina of an eye with light is performed with light at an exposure on the eye below about 10 $mJ/cm^2$.

3. The method of claim 1, wherein illuminating the macula and adjacent peripheral retina of an eye with light comprises illuminating the macula and adjacent peripheral retina of a living undilated eye.

4. The method for diagnosing a subject, comprising: performing the method of claim 1 upon the eye of a subject, comparing macular pigment levels to correlative data indicative of one or more pathologies or symptoms, and based upon the comparison, determining the presence, absence or degree of one or more pathologies or symptoms.

5. The method of claim 1, wherein illuminating the macula and peripheral retina of an eye with light is performed with light at a wavelength of from about 450 nm to about 500 nm.

6. The method of claim 1, wherein illuminating the macular and adjacent peripheral retinal tissue of an eye is performed for a period of less than about 200 milliseconds.

7. A method for measuring macular pigment, comprising:
   directing light from a light source onto the macula and adjacent peripheral retinal area of a living eye;
   collecting light emitted from the macula and adjacent peripheral retina at a wavelength range that is outside the emission range of interfering fluorophores,
   quantifying the collected light in the macular tissue and adjacent peripheral retinal tissue thereby quantifying lipofuscin emission intensities; and
   determining macular pigment levels in the macular tissue from the differing lipofuscin emission intensities in both the macula and adjacent peripheral retina.

8. The method of claim 7, wherein the collected light is filtered such that only light above about 700 nm is quantified.

9. The method of claim 7, wherein the light from the light source has an intensity that does not substantially alter macular pigment levels in the macular tissue.

10. The method of claim 7, wherein the light source generates light at a wavelength of from about 450 nm to about 500 nm.

11. The method of claim 7, wherein the light source generates laser light at a wavelength of about 488 nm.

12. The method of claim 7, wherein the light source is a light emitting diode.

13. The method of claim 7, wherein the light exposure from the light source on the eye is below about 10 mJ/cm$^2$.

14. The method of claim 7, wherein the collected light is used to produce digital images representing the concentration levels of macular pigment at a plurality of points in the macular tissue.

15. The method of claim 14, further comprising determining spatial extent and topographic concentration distribution of the macular pigment from the digital images.

16. The method of claim 7, wherein the lipofuscin emission originates from lipofuscin that is located in the retinal pigment epithelium of the eye.

17. A method for diagnosing a subject, comprising: performing the method of claim 7 upon the eye of the subject; comparing the macular pigment levels to correlative data indicative of one or more pathologies or symptoms; and based upon the comparison, determining the presence, absence, or degree of one or more pathologies or symptoms.

18. The method of claim 7, wherein determining macular pigment levels in macular tissue from the differing lipofuscin emission intensities in the macula and adjacent peripheral retina is performed by determining log differences of foveal and perifoveal fluorescence densities.

* * * * *

UNITED STATES PATENT AND TRADEMARK OFFICE
CERTIFICATE OF CORRECTION

PATENT NO. : 8,326,405 B2
APPLICATION NO. : 13/316364
DATED : December 4, 2012
INVENTOR(S) : Werner Gellermann et al.

Page 1 of 1

It is certified that error appears in the above-identified patent and that said Letters Patent is hereby corrected as shown below:

In the Specification

In column 1, line 16, please delete "for Macular Tissue" and replace it with --in Macular Tissue--.

Signed and Sealed this
Fifteenth Day of October, 2013

Teresa Stanek Rea
*Deputy Director of the United States Patent and Trademark Office*